(12) United States Patent
Izumi

(10) Patent No.: US 11,270,413 B2
(45) Date of Patent: Mar. 8, 2022

(54) PLAYBACK APPARATUS AND METHOD, AND GENERATION APPARATUS AND METHOD

(71) Applicant: SONY CORPORATION, Tokyo (JP)

(72) Inventor: Nobuaki Izumi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 114 days.

(21) Appl. No.: 16/755,731

(22) PCT Filed: Oct. 5, 2018

(86) PCT No.: PCT/JP2018/037328
§ 371 (c)(1),
(2) Date: Apr. 13, 2020

(87) PCT Pub. No.: WO2019/078033
PCT Pub. Date: Apr. 25, 2019

(65) Prior Publication Data
US 2020/0334788 A1    Oct. 22, 2020

(30) Foreign Application Priority Data

Oct. 20, 2017   (JP) .............................. JP2017-203234

(51) Int. Cl.
*G06T 3/40* (2006.01)
*G02B 27/00* (2006.01)
(Continued)

(52) U.S. Cl.
CPC ........ *G06T 3/4038* (2013.01); *G02B 27/0093* (2013.01); *G02B 27/0172* (2013.01);
(Continued)

(58) Field of Classification Search
CPC ....... G06T 3/4038; G06T 15/20; G06T 17/10; G02B 27/0093; G02B 27/0172
See application file for complete search history.

(56) References Cited

U.S. PATENT DOCUMENTS

2003/0095131 A1* 5/2003 Rondinelli ............ G06T 3/0062
345/582
2003/0228070 A1* 12/2003 Miki ......................... G06T 7/74
382/289
(Continued)

FOREIGN PATENT DOCUMENTS

JP     2003-132348 A    5/2003
JP     2004-013326 A    1/2004
(Continued)

*Primary Examiner* — Sarah Lhymn
(74) *Attorney, Agent, or Firm* — Paratus Law Group, PLLC

(57) ABSTRACT

There is provided a playback apparatus and method, and generation apparatus and method capable of performing enlargement/reduction display of an image while preventing an occurrence of motion sickness. In a case where enlargement/reduction of omnidirectional image is selected, the playback apparatus includes a vertex data transformer that generates a 3D model for enlargement/reduction. The present disclosure can be applied, for example, to a playback apparatus and the like that generates an image obtained by perspective-projecting an omnidirectional image as a display image according to the viewer/listener's line-of-sight direction.

9 Claims, 26 Drawing Sheets

(51) Int. Cl.
   *G02B 27/01* (2006.01)
   *G06T 15/20* (2011.01)
   *G06T 17/10* (2006.01)

(52) U.S. Cl.
   CPC .............. *G06T 15/20* (2013.01); *G06T 17/10* (2013.01); *G02B 2027/014* (2013.01); *G02B 2027/0187* (2013.01)

(56) References Cited

U.S. PATENT DOCUMENTS

| | | | |
|---|---|---|---|
| 2019/0253734 A1* | 8/2019 | Lee | H04N 5/23238 |
| 2019/0373245 A1* | 12/2019 | Lee | H04N 13/194 |
| 2019/0387212 A1* | 12/2019 | Oh | G06T 3/0018 |

FOREIGN PATENT DOCUMENTS

| | | |
|---|---|---|
| JP | 2013-012893 A | 1/2013 |
| JP | 2015-125502 A | 7/2015 |
| JP | 2016-024751 A | 2/2016 |
| WO | WO 2016/013272 A1 | 1/2016 |
| WO | WO 2016/140060 A1 | 9/2016 |

\* cited by examiner

FIG. 7

| $x_0$ | $y_0$ | $z_0$ | $u_0$ | $v_0$ |
|---|---|---|---|---|
| $x_1$ | $y_1$ | $z_1$ | $u_1$ | $v_1$ |
| $x_2$ | $y_2$ | $z_2$ | $u_2$ | $v_2$ |
| ⋮ | | | | |
| $x_{N-1}$ | $y_{N-1}$ | $z_{N-1}$ | $u_{N-1}$ | $v_{N-1}$ |

FIG. 23

| ID | AZIMUTH ANGLE | ELEVATION ANGLE | ROTATION ANGLE | ENLARGEMENT FACTOR |
|---|---|---|---|---|
| 1 | 0° | 0° | 0° | 1.0 |
| 2 | 0° | 0° | 0° | 2.0 |
| 3 | +90° | 0° | 0° | 2.0 |
| 4 | +180° | 0° | 0° | 2.0 |
| 5 | −90° | 0° | 0° | 2.0 |

PLAYBACK APPARATUS AND METHOD, AND GENERATION APPARATUS AND METHOD

CROSS REFERENCE TO PRIOR APPLICATION

This application is a National Stage Patent Application of PCT International Patent Application No. PCT/JP2018/037328 (filed on Oct. 5, 2018) under 35 U.S.C. § 371, which claims priority to Japanese Patent Application No. 2017-203234 (filed on Oct. 20, 2017), which are all hereby incorporated by reference in their entirety.

TECHNICAL FIELD

The present disclosure relates to playback apparatuses and methods, and generation apparatuses and methods. In particular, the present disclosure relates to a playback apparatus and method, and generation apparatus and method capable of performing enlargement/reduction display of an image while preventing an occurrence of motion sickness.

BACKGROUND ART

An entire celestial-sphere image or omnidirectional image, which allows looking around any direction, is obtained by recording light rays incident on one point in all directions as a pixel value such as RGB. This pixel value is typically recorded as a planar rectangular image such as equirectangular projection. Upon playback, this planar rectangular image is affixed to a virtual unit spherical surface and rendering is performed to look around from the center of the sphere, which enables the original light ray direction and RGB values to be reproduced.

The above-mentioned omnidirectional image is obtained by recording light rays incident on one point, so images from different viewpoints fail to be reproduced and only the rotational movement using the center of the sphere as a reference is reproducible. As the degree of freedom, only three degrees of freedom of the rotational component is achievable among the six degrees of freedom in total including three degrees of freedom of yaw, pitch and row corresponding to rotation and three degrees of freedom of x, y and z corresponding to motion, and so it is called three degrees of freedom (3DoF) omnidirectional images in some cases.

Examples of ways of displaying this 3DoF omnidirectional image include a way of displaying it on a stationary display such as a television set and viewing/listening while changing the display direction using a controller, a way of displaying it on the screen of a mobile terminal held in the hand while changing the display direction on the basis of the attitude information obtained from a built-in gyro sensor of the terminal, or a way of displaying it on a head-mounted display (hereinafter, also referred to as an HMD) mounted on the head while reflecting the display direction in the movement of the head.

The 3DoF omnidirectional image does not have the freedom of motion from one point in an image, so an operation for making the image look closer fails to be performed. However, there is a demand for allowing viewing by enlarging an image like a telescope so that the details are recognizable.

In a flat display of a television set, a mobile terminal, or the like, it is possible to perform an enlargement operation by changing a display angle of view (or field of view (FOV)). In image viewing/listening through a normal flat display, it is general that the shooting angle of view and the display angle of view may not be necessarily coincident with each other, so less discomfort is experienced even in a case of changing the display angle of view.

On the other hand, the HMD is worn on the head, so the display angle of view during viewing/listening is basically fixed. In addition, a typical HMD is equipped with a sensor for detecting the movement of the viewer/listener's head, and the HMD performs image display obtained by reflecting the viewer/listener's line of sight or position. Only the rotational movement is reproducible in the 3DoF omnidirectional image, but by precisely matching this rotational movement with the head's rotational movement, it is possible to experience an immersive feeling as if being entered a virtual world.

In this description, in a case where an enlargement/reduction operation (zoom operation) is performed on an image viewed through the HMD by simply changing the angle of view and enlarging it in the same way as a flat display, the head's rotation angle and the image's rotation angle do not match. In one example, upon enlargement, the image appears to move faster than the head's rotation by the enlarged size of the image. This causes discomfort, which leads to an unpleasant feeling called VR motion sickness or the like in many cases.

In one example, Patent Documents 1 and 2 disclose an example of changing the angle of view of a display image in the HMD.

CITATION LIST

Patent Document

Patent Document 1: Japanese Patent Application Laid-Open No. 2015-125502
Patent Document 2: Japanese Patent Application Laid-Open No. 2016-24751

SUMMARY OF THE INVENTION

Problems to be Solved by the Invention

Patent Documents 1 and 2 however do not teach any countermeasure for a phenomenon in which the head's rotation angle does not match the image's rotation angle and so the problem of motion sickness fails to be fundamentally solved.

The present disclosure is made in view of such a situation, and it is intended to be capable of performing the enlargement/reduction display of an image in which an occurrence of motion sickness is prevented.

Solutions to Problems

A playback apparatus according to a first aspect of the present disclosure includes a 3D model generation unit configured to generate a 3D model for enlargement/reduction in a case of selecting enlargement/reduction of a wide-angle image.

A playback method according to the first aspect of the present disclosure includes generating, by a playback apparatus, a 3D model for enlargement/reduction in a case of selecting enlargement/reduction of a wide-angle image.

According to the first aspect of the present disclosure, the 3D model for enlargement/reduction is generated in a case of selecting enlargement/reduction of a wide-angle image.

A generation apparatus according to a second aspect of the present disclosure includes a wide-angle image generation unit configured to generate a wide-angle image mapped to a predetermined 3D model for use in a playback apparatus including a 3D model generation unit configured to generate a 3D model for enlargement/reduction in a case of selecting enlargement/reduction of the wide-angle image.

A generation method according to the second aspect of the present disclosure includes generating, by a generation apparatus, a wide-angle image mapped to a predetermined 3D model for use in a playback apparatus including a 3D model generation unit configured to generate a 3D model for enlargement/reduction in a case of selecting enlargement/reduction of the wide-angle image.

According to the second aspect of the present disclosure, a wide-angle image mapped to a predetermined 3D model for use in a playback apparatus including a 3D model generation unit configured to generate a 3D model for enlargement/reduction is generated in a case of selecting enlargement/reduction of the wide-angle image.

Moreover, the playback apparatus according to the first aspect and the generation apparatus according to the second aspect of the present disclosure can be implemented by causing a computer to execute a program.

Further, the program executed by the computer to implement the playback apparatus according to the first aspect and the generation apparatus according to the second aspect of the present disclosure can be provided by being transmitted via a transmission medium or by being recorded on a recording medium.

The playback apparatus and the generation apparatus can be independent apparatuses or can be internal modules that constitute a single device.

Effects of the Invention

According to the first aspect of the present disclosure, it is possible to perform the enlargement/reduction display of an image in which an occurrence of motion sickness is prevented.

According to the second aspect of the present disclosure, it is possible to generate an image used to perform the enlargement/reduction display of an image in which an occurrence of motion sickness is prevented.

Note that the advantageous effects described here are not necessarily limiting and any advantageous effect described in the present disclosure may be obtained.

BRIEF DESCRIPTION OF DRAWINGS

FIG. 7 is a diagram illustrating vertex array data of a 3D mesh model.

FIG. 23 is a diagram illustrating an example of a table as auxiliary information generated by a table generation unit.

MODE FOR CARRYING OUT THE INVENTION

The modes for carrying out the technology of the present disclosure (hereinafter referred to as embodiments) are now described. Meanwhile, the description will be given in the following order.

1. First embodiment (exemplary configuration using only omnidirectional image having uniform resolution)
2. Second embodiment (exemplary configuration in which omnidirectional image having high-resolution direction is switched and used)
3. Other modifications
4. Computer configuration example

1. First Embodiment (Exemplary Configuration of Delivery System According to First Embodiment)

Figure 1:
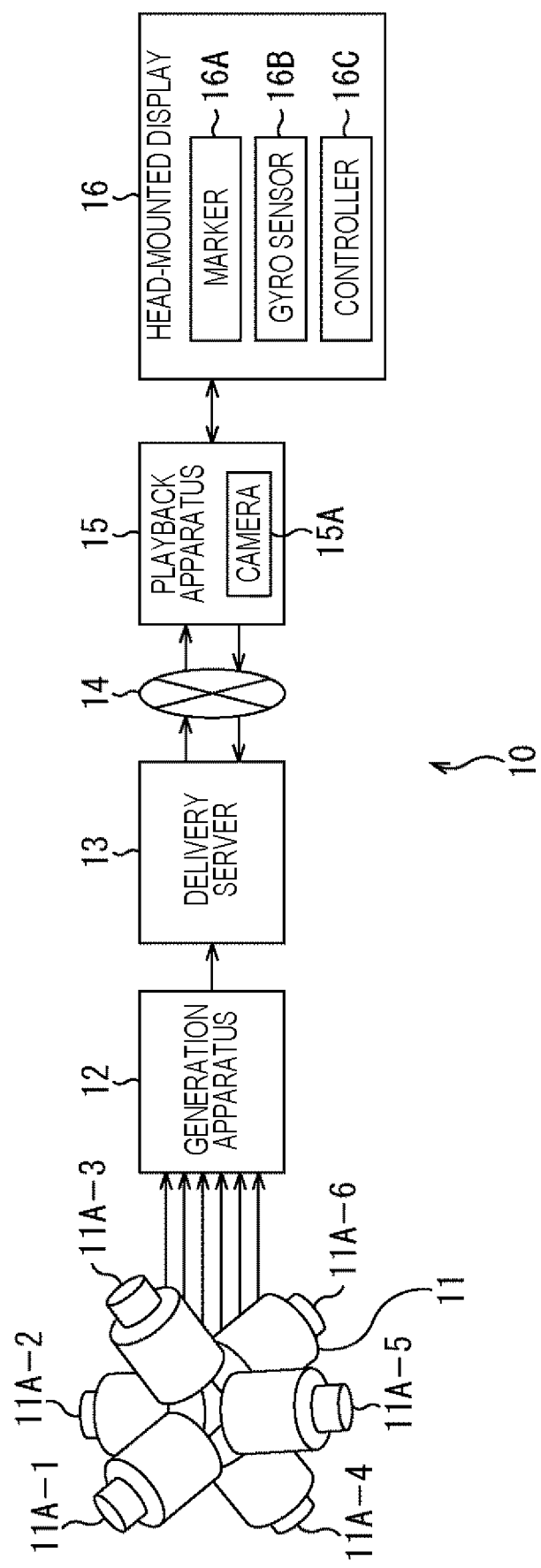
FIG. 1 is a block diagram illustrating an exemplary configuration of a delivery system of a first embodiment to which the present disclosure is applied.

FIG. 1 is a block diagram illustrating an exemplary configuration of a delivery system according to a first embodiment to which the technology of the present disclosure is applied.

A delivery system 10 in FIG. 1 includes an imaging apparatus 11, a generation apparatus 12, a delivery server 13, a network 14, a playback apparatus 15, and a head-mounted display 16. The delivery system 10 generates an omnidirectional image from a captured image taken by the imaging apparatus 11 and displays a display image of a viewer/listener's field of view using the omnidirectional image.

Specifically, the imaging apparatus 11 of the delivery system 10 has six cameras 11A-1 to 11A-6. Moreover, the cameras 11A-1 to 11A-6 are hereinafter referred to as the camera 11A unless it is necessary to particularly distinguish them.

The respective cameras 11A capture a moving image. The imaging apparatus 11 supplies the moving images in six directions captured by the respective cameras 11A to the generation apparatus 12 as captured images. Moreover, the number of cameras provided in the imaging apparatus 11 is not limited to six as long as it is plural.

The generation apparatus 12 generates an omnidirectional image of all-around 360 degrees in the horizontal direction and 180 degrees in the perpendicular direction from the captured image supplied from the imaging apparatus 11 by a technique using the equirectangular projection. The generation apparatus 12 performs compression-encoding of image data, which is obtained by mapping an omnidirectional image capable of looking around 360 degrees in all directions of up, down, left, and right using the equirectangular projection to a predetermined 3D model, by a predetermined encoding scheme such as advanced video coding (AVC) or high-efficiency video coding (HEVC)/H.265. The generation apparatus 12 uploads an encoded stream obtained by performing the compression-encoding on the image data of the omnidirectional image to the delivery server 13.

The delivery server 13 is connected with the playback apparatus 15 via the network 14. The delivery server 13 stores the encoded stream of the omnidirectional image uploaded from the generation apparatus 12. The delivery server 13 transmits the stored encoded stream of the omnidirectional image to the playback apparatus 15 via the network 14 in response to a request from the playback apparatus 15.

The playback apparatus 15 requests and receives the encoded stream of the omnidirectional image from the delivery server 13. The playback apparatus 15 generates a 3D model image by decoding the encoded stream of the received omnidirectional image and mapping the resulting omnidirectional image to a predetermined 3D model.

Then, the playback apparatus 15 generates an image in a viewer/listener's field of view as a display image by perspective-projecting the 3D model image onto the viewer/listener's field of view with the viewing/listening position as the focal point. The playback apparatus 15 supplies the generated display image to the head-mounted display 16.

Figure 2:
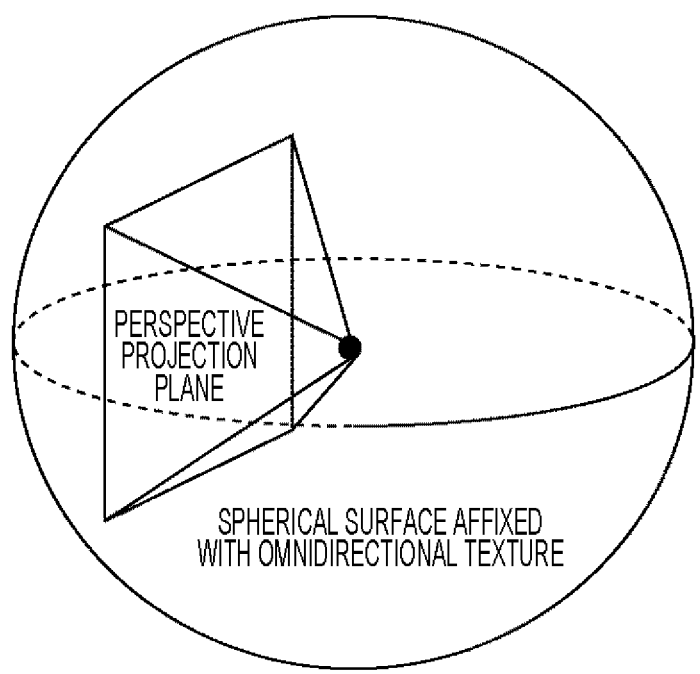
FIG. 2 is a conceptual diagram of a rendering method in a case where a spherical surface is used as a 3D model used for mapping an omnidirectional image.

FIG. 2 is a conceptual diagram of a rendering method in a case where a spherical surface is used as a 3D model used for mapping an omnidirectional image.

The spherical surface is used as a 3D model, the texture of the omnidirectional image obtained by the equirectangular projection is affixed onto the coordinates on the spherical surface corresponding to the latitude and longitude of the earth, the center of the sphere is set as the viewing/listening position, and the omnidirectional image (3D model image) on the spherical surface is perspective-projected in the viewer/listener's field of view.

Moreover, the rendering method using the 3D model is an example, and there is also a technique of rendering by directly calculating the two-dimensional coordinates of the texture by following the light rays on the projection surface rather than actually creating the 3D model. Even in the case of directly calculating and rendering the two-dimensional coordinates of the texture, the processing to be implemented is similarly performed and intuitive awareness is possible by setting a virtual 3D model.

The viewer/listener's field of view is determined on the basis of the result obtained by capturing an image of a marker 16A attached to the head-mounted display 16 and the result detected by a gyro sensor 16B of the head-mounted display 16.

In other words, the playback apparatus 15 has a built-in camera 15A that captures an image of the marker 16A attached to the head-mounted display 16. Then, the playback apparatus 15 detects the viewer/listener's viewing/listening position in the coordinate system of the 3D model (hereinafter referred to as a 3D model coordinate system) on the basis of the image obtained by capturing an image of the marker 16A. Furthermore, the playback apparatus 15 receives the result, which is detected by the gyro sensor 16B of the head-mounted display 16, from the head-mounted display 16. The playback apparatus 15 determines a line-of-sight direction of the viewer/listener in the 3D model coordinate system on the basis of the detection result of the gyro sensor 16B. The playback apparatus 15 determines the field of view of the viewer/listener located inside the 3D model on the basis of the viewing/listening position and the line-of-sight direction.

Further, the viewer/listener is able to instruct a controller 16C attached to the head-mounted display 16 so that the display image displayed on the head-mounted display 16 is enlarged or shrunk by operating the controller 16C.

The playback apparatus 15 receives zoom operation information that is associated with an enlargement/reduction operation performed by the viewer/listener from the head-mounted display 16, and enlarges or reduces a display image to be displayed on the head-mounted display 16 in response to the zoom operation performed by the viewer/listener.

The head-mounted display 16 is mounted on the viewer/listener's head and displays the display image supplied from the playback apparatus 15. The head-mounted display 16 is provided with the marker 16A to be imaged by the camera 15A. Thus, the viewer/listener is able to specify the viewing/listening position with the motion while the head-mounted display 16 is mounted on the head. In addition, the head-mounted display 16 has the built-in gyro sensor 16B for detecting the angular velocity and transmits the detection result by the gyro sensor 16B to the playback apparatus 15. Thus, the viewer/listener is able to specify the line-of-sight direction by turning the head on which the head-mounted display 16 is mounted.

Further, the head-mounted display 16 detects the zoom operation performed by the viewer/listener by operating the controller 16C and supplies the zoom operation information to the playback apparatus 15.

The delivery system 10 can employ any technique as the delivery technique from the delivery server 13 to the playback apparatus 15. In a case where the delivery technique is, in one example, the moving picture experts group phase-dynamic adaptive streaming over HTTP (MPEG-DASH) technique, the delivery server 13 corresponds to a hypertext transfer protocol (HTTP) server, and the playback apparatus 15 corresponds to an MPEG-DASH client.

(Configuration Example of Generation Apparatus)

Figure 3:
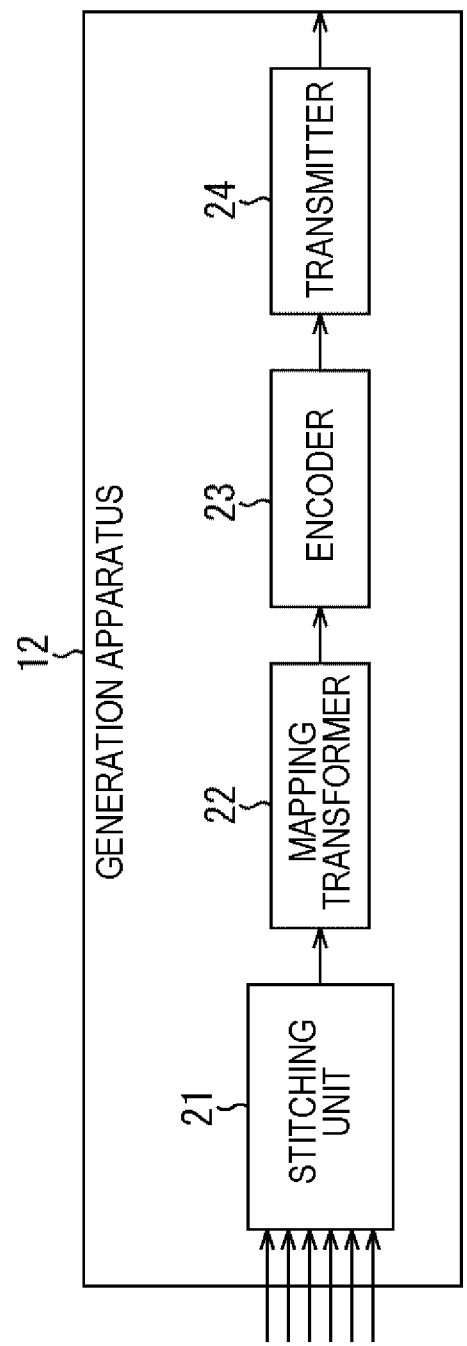
FIG. 3 is a block diagram illustrating an exemplary configuration of a generation apparatus in FIG. 1.

FIG. 3 is a block diagram illustrating an exemplary configuration of the generation apparatus 12 in FIG. 1.

In FIG. 3, the generation apparatus 12 includes a stitching unit 21, a mapping transformer 22, an encoder 23, and a transmitter 24.

The stitching unit 21 makes colors or brightness of the captured images in six directions supplied from the cameras 11A in FIG. 1 identical for each frame, removes overlaps to connect, and transforms them into one captured image with sufficient resolution. In one example, the stitching unit 21 performs the transformation into an equirectangular image as the single captured image. The stitching unit 21 supplies an equirectangular image, which is a captured image in frame units, to the mapping transformer 22.

The mapping transformer 22 (wide-angle image generation unit) performs mapping transformation processing of transforming a captured image (e.g., an equirectangular image) in frame units supplied from the stitching unit 21 into a mapping format for mapping to a predetermined 3D model. As the predetermined 3D model, in one example, a cubic model, a spherical model, or the like can be employed.

In a case where, in one example, a cubic model is employed as the 3D model and the omnidirectional image is delivered, the mapping transformer 22 transforms the equirectangular omnidirectional image from the stitching unit 21 into a mapping format for a cubic model (a format illustrated in FIG. 6 described later). In a case where a mapping format of the omnidirectional image supplied from the stitching unit 21 is the same as a mapping format upon being supplied to the delivery server 13, mapping transformation processing is unnecessary.

In the present embodiment, the 3D model used in the playback apparatus 15 is a spherical model, and the mapping format corresponding to the 3D model is the equirectangular mapping, so mapping transformation processing is unnecessary.

The encoder 23 (encoding unit) encodes the omnidirectional image supplied from the mapping transformer 22 using a predetermined encoding scheme such as MPEG-2 or AVC standard to generate an encoded stream. The encoder 23 supplies one encoded stream being generated to the transmitter 24. Moreover, the encoded stream of the omnidirectional image can be multiplexed together with an audio signal in a system layer format of an MP4 file or the like.

The transmitter 24 uploads (transmits) the omnidirectional image streams supplied from the encoder 23 to the delivery server 13 in FIG. 1.

(Exemplary Configuration of Delivery Server and Playback Apparatus)

Figure 4:
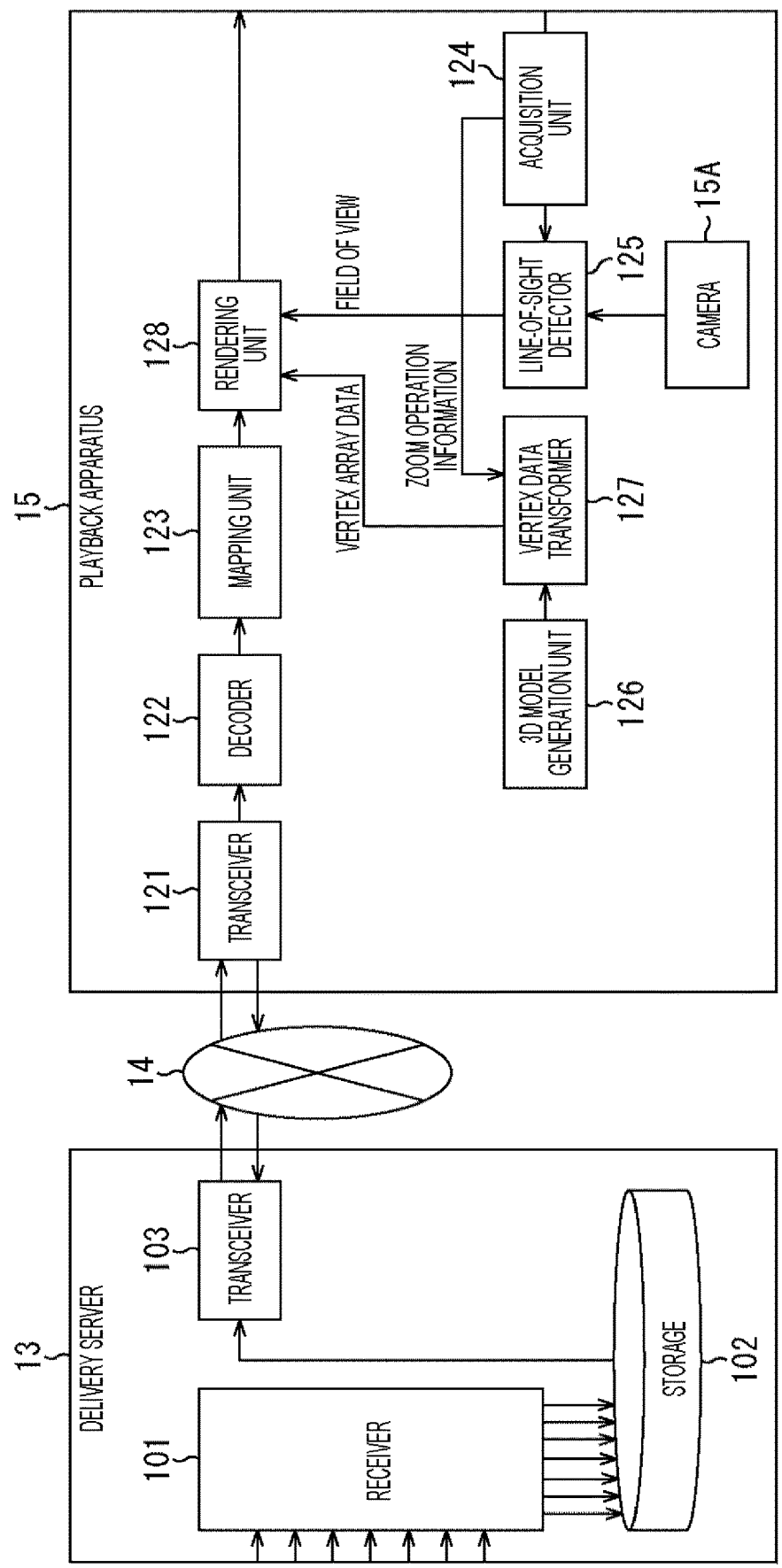
FIG. 4 is a block diagram illustrating an exemplary configuration of a delivery server and a playback apparatus in FIG. 1.

FIG. 4 is a block diagram illustrating an exemplary configuration of the delivery server 13 and the playback apparatus 15 in FIG. 1.

The delivery server 13 includes a receiver 101, a storage 102, and a transceiver 103.

The receiver 101 receives the encoded stream of the omnidirectional image uploaded from the generation apparatus 12 in FIG. 1 and supplies it to the storage 102.

The storage 102 stores the encoded stream of the omnidirectional image supplied from the receiver 101.

The transceiver 103 reads the encoded stream of the omnidirectional image stored in the storage 102 and transmits it to the playback apparatus 15 via the network 14 in response to a request from the playback apparatus 15.

The playback apparatus 15 includes the camera 15A, a transceiver 121, a decoder 122, a mapping unit 123, an acquisition unit 124, a line-of-sight detector 125, a 3D model generation unit 126, a vertex data transformer 127, and a rendering unit 128.

The transceiver 121 (acquisition unit) of the playback apparatus 15 requests the omnidirectional image from the delivery server 13 via the network 14 and acquires the encoded stream of the omnidirectional image to be transmitted from the transceiver 103 of the delivery server 13 in response to the request. The transceiver 121 supplies the obtained encoded stream of the omnidirectional image to the decoder 122.

The decoder 122 (decoding unit) decodes the encoded stream to be supplied from the transceiver 121 to generate an omnidirectional image. The decoder 122 supplies the generated omnidirectional image to the mapping unit 123.

The mapping unit 123 generates texture data (R, G, B) corresponding to texture coordinates (u, v) of a predetermined 3D model by using the omnidirectional image supplied from the decoder 122. In this description, the 3D model used in the playback apparatus 15 corresponds to the 3D model used in the generation apparatus 12, and in the present embodiment, a spherical model is assumed to be used as the 3D model as described above, but the 3D model is not limited to this example and can be, in one example, a cubic model.

Figure 5:
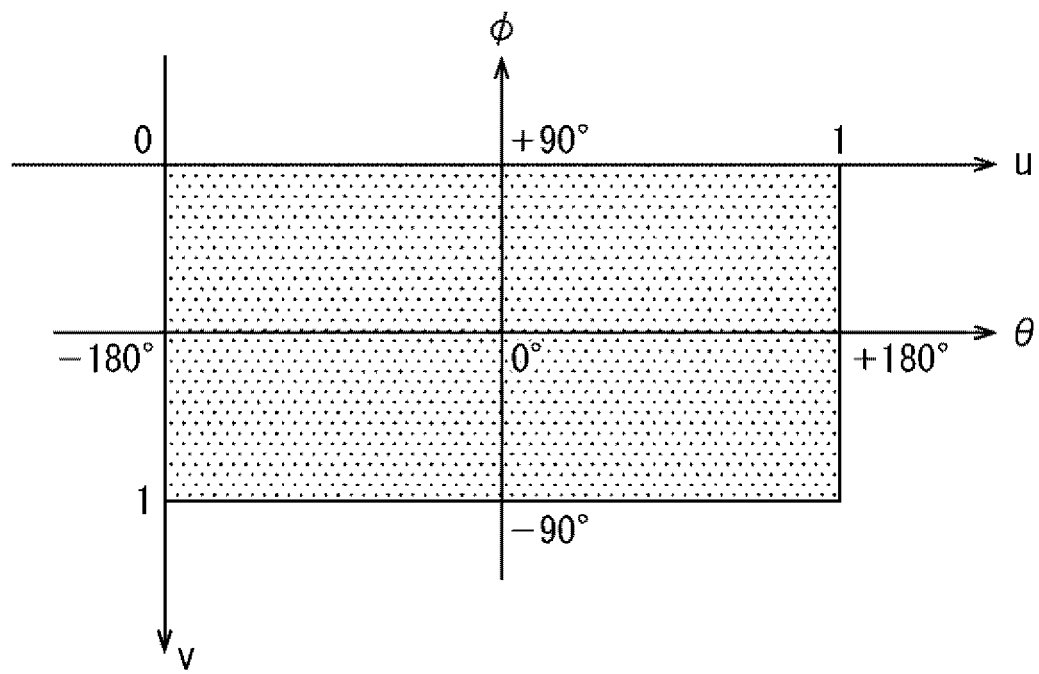
FIG. 5 is a diagram illustrating a relationship between polar coordinates and texture coordinates of an equirectangular mapping texture.

FIG. 5 illustrates the relationship between polar coordinates and texture coordinates of equirectangular mapping texture upon affixing a texture to a spherical 3D model.

The u-axis of the texture coordinates (u, v) is defined as parallel to the azimuth angle (rotation angle) e of the polar coordinates, and the v-axis of the texture coordinates (u, v) is defined as parallel to the elevation angle φ of the polar coordinates. The value of the texture coordinates (u, v) is a value in the range of 0 to 1.

Figure 6:
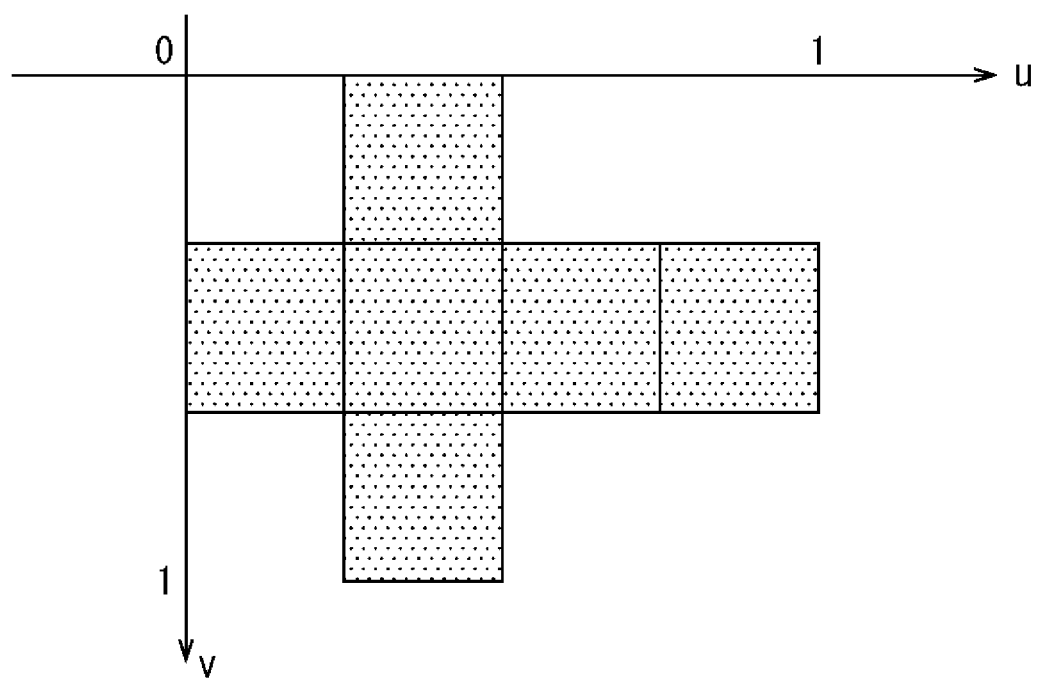
FIG. 6 is a diagram illustrating an example of texture coordinates in affixing texture on a 3D model of a cube.

FIG. 6 illustrates an example of texture coordinates (u, v) in affixing texture on a 3D model of a cube.

The texture data generated by the mapping unit 123 is supplied to the rendering unit 128 by being stored in a texture buffer accessible by the rendering unit 128.

The acquisition unit 124 acquires the detection result of the gyro sensor 16B in FIG. 1 from the head-mounted display 16 and supplies the result to the line-of-sight detector 125.

Further, the acquisition unit 124 acquires zoom operation information associated with the zoom operation performed by the viewer/listener who operates the controller 16C from the head-mounted display 16, and supplies the information to the vertex data transformer 127.

The line-of-sight detector 125 determines the viewer/listener's line-of-sight direction in the 3D model coordinate system on the basis of the detection result of the gyro sensor 16B that is supplied from the acquisition unit 124. In addition, the line-of-sight detector 125 acquires the captured image of the marker 16A from the camera 15A and detects the viewing/listening position in the coordinate system of the 3D model on the basis of the captured image. Then, the line-of-sight detector 125 determines the viewer/listener's field of view in the 3D model coordinate system on the basis of the viewing/listening position and the line-of-sight direction in the 3D model coordinate system. The line-of-sight detector 125 supplies the viewer/listener's field of view and viewing/listening position to the rendering unit 128.

The 3D model generation unit 126 generates data of a 3D mesh model (3D model) in a virtual 3D space and supplies the data to the vertex data transformer 127. This data of the 3D mesh model includes five-element array data of the coordinates (x, y, z) of each vertex of the 3D model and texture coordinates (u, v) corresponding thereto (hereinafter referred to as "vertex array data") as illustrated in FIG. 7. In the present embodiment, the same spherical model as the 3D model used in the generation apparatus 12 is employed as the 3D model.

Figure 8:
FIG. 8 is a diagram illustrated to describe transformation of vertex array data by vertex data transformation processing.

The vertex data transformer 127 performs the transformation of the vertex array data of the spherical model supplied from the 3D model generation unit 126 on the basis of the zoom operation information supplied from the acquisition unit 124. Specifically, as illustrated in FIG. 8, the coordinates (x, y, z) of the vertex of the 3D mesh model are transformed into coordinates (x', y', z'), and the vertex array data that is constituted by five elements of the transformed coordinates (x', y', z') of each vertex and the texture coordinates (u, v) corresponding thereto is supplied to the rendering unit 128. In other words, the vertex data transformer 127 is an enlargement/reduction 3D model generation unit that generates 3D mesh model data for enlargement/reduction on the basis of the zoom operation information from the 3D mesh model data generated by the 3D model generation unit 126. The details of the vertex data transformation processing performed by the vertex data transformer 127 will be described later with reference to FIG. 9 and the subsequent drawings.

The rendering unit 128 is supplied with the texture data (R, G, B) corresponding to the texture coordinates (u, v) from the mapping unit 123 and is supplied with the vertex array data that is constituted by five elements of the coordinates (x', y', z') of each vertex of the spherical model and the texture coordinates (u, v) corresponding thereto from the vertex data transformer 127. In addition, the rendering unit 128 is also supplied with the viewer/listener's field of view and viewing/listening position from the line-of-sight detector 125.

The rendering unit 128 displays, as a display image, an image of the viewer/listener's field of view in a spherical model on which an omnidirectional image is mapped using the five-element vertex array data, the texture data, and the viewer/listener's field of view and viewing/listening position.

In FIG. 8, each row is vertex data corresponding to one vertex, and one triangular patch is constituted by three vertex data elements. The association between the coordinates (x, y, z) in the 3D space and the texture coordinates (u, v) is kept for the vertices of the triangular patch, so the triangle on the texture is affixed to the triangle on the spherical model by homography transformation, and the resultant is rendered to look around from the inside of the spherical model, which makes it possible to display a looking-around image of the celestial sphere.

(Configuration Example of Vertex Data Transformer)

Figure 9:
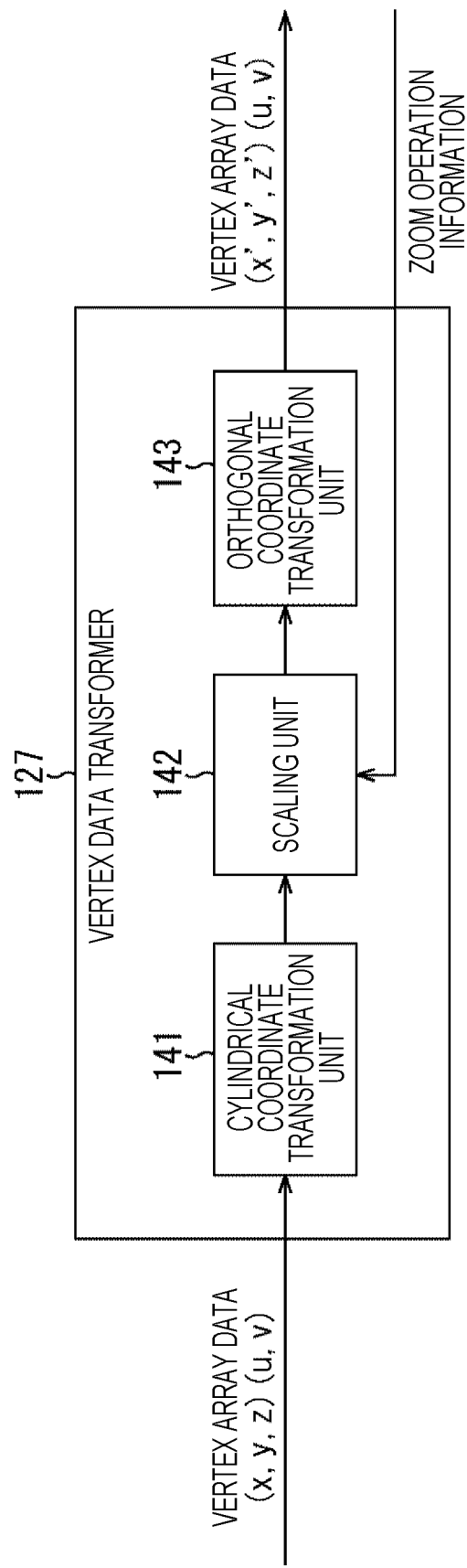
FIG. 9 is a block diagram illustrating a specific exemplary configuration of a vertex data transformer in FIG. 4.

FIG. 9 is a block diagram illustrating a specific exemplary configuration of a vertex data transformer 127.

The vertex data transformer 127 includes a cylindrical coordinate transformation unit 141, a scaling unit 142, and an orthogonal coordinate transformation unit 143.

The vertex data transformer 127 transforms the vertex array data represented in the xyz-orthogonal coordinate system into a cylindrical coordinate system and performs scaling (enlargement or reduction) based on the zoom operation information on the cylindrical coordinate system. Then, the vertex data transformer 127 returns the scaled data to the orthogonal coordinate system again and outputs it.

The cylindrical coordinate transformation unit 141 transforms the vertex array data represented in the orthogonal coordinate system into the cylindrical coordinate system. The vertex array data is constituted by five-element data of the coordinates (x, y, z) of each vertex of the spherical model and its corresponding texture coordinates (u, v).

The correspondence relationship between the orthogonal coordinate system and the cylindrical coordinate system is expressed by Formula (1) below.

[Math. 1]

$$\begin{pmatrix} x \\ y \\ z' \end{pmatrix} = \begin{pmatrix} t\cos\theta \\ t\sin\theta \\ z \end{pmatrix} \quad (1)$$

Figure 10:
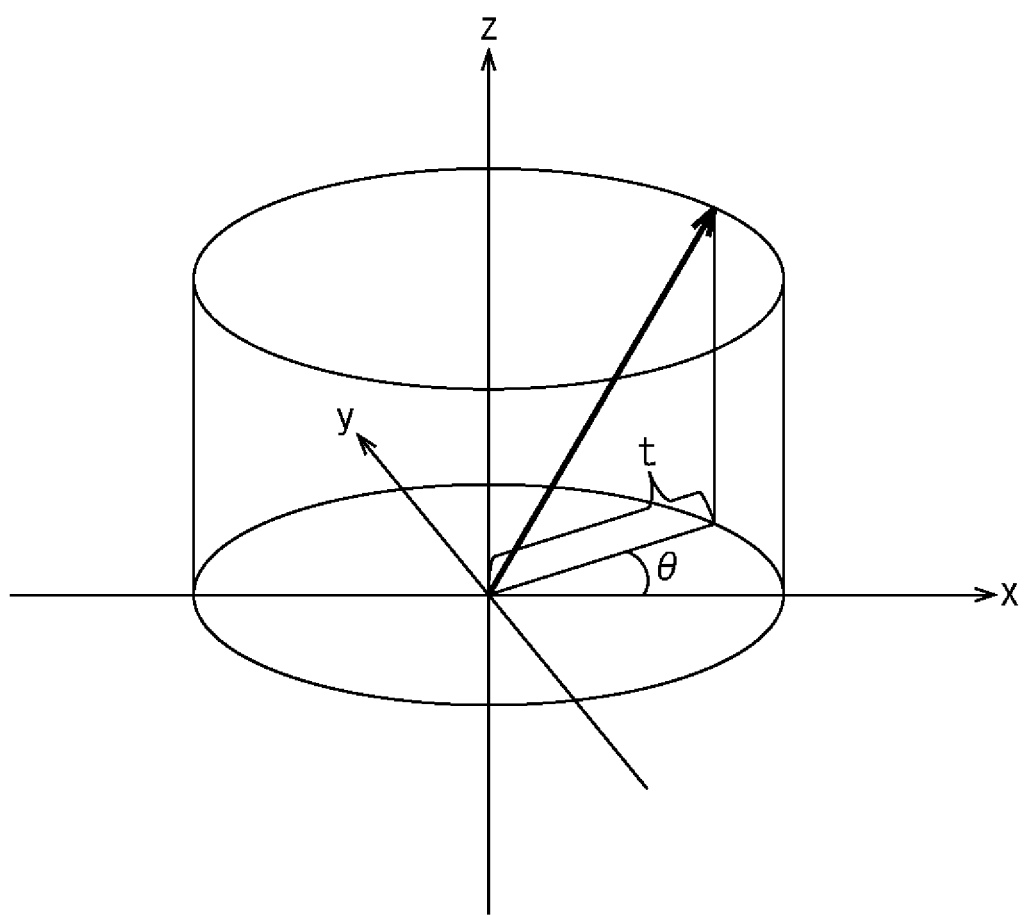
FIG. 10 is a diagram illustrating a relationship between an orthogonal coordinate system and a cylindrical coordinate system in a three-dimensional space.

FIG. 10 illustrates the relationship between the orthogonal coordinate system (x, y, z) and the cylindrical coordinate system (t, θ, z) in a three-dimensional space. In this case, Formula (2) is established from the definition of the trigonometric function.

[Math. 2]

$$t = \sqrt{x^2 + y^2} \quad (2)$$

The direction of gravity is important for viewing/listening on the head-mounted display 16, so the vertex data transformer 127 sets the z-axis of the orthogonal coordinate system (x, y, z) to the vertical direction. In this case, the plane at z=0 is a horizontal plane such as the ground, and θ in the cylindrical coordinate system represents the azimuth angle.

The zoom operation information supplied from the head-mounted display 16 is acquired by the scaling unit 142.

The scaling unit 142 performs the scaling (enlargement or reduction) based on the zoom operation information by performing a mapping transformation $f_k$ that multiplies the coordinates (x, y, z) of each vertex of the spherical model transformed on the cylindrical coordinate system by k.

Assuming that the coordinates (x, y, z) on the orthogonal coordinate system are transformed into coordinates (x', y', z') by the mapping transformation $f_k$, the relationship between the coordinates (x, y, z) and the coordinates (x', y', z') is expressed as follows.

$$(x', y', z') = f_k(x, y, z) \quad (3)$$

Further, assuming that the coordinates (t, θ, z) on the cylindrical coordinate system are transformed into coordinates (t', θ', z') by the mapping transformation $f_k$, the relationship between the coordinates (t, θ, z) and the coordinates (t', θ', z') is expressed as follows.

$$(t', \theta', z') = f_k(t, \theta, z) \quad (4)$$

The specific processing of the mapping transformation $f_k$ is expressed by Formulas (5) to (7) below.

$$t' = t \quad (5)$$

$$\theta' = k\theta \quad (6)$$

$$z' = kz \quad (7)$$

In other words, the mapping transformation $f_k$ is obtained by independently scaling the axis of the cylindrical coordinate system, and is processing of multiplying the azimuth angle θ by k and multiplying the vertical direction z by k.

The transformed coordinates (x', y', z') on the orthogonal coordinate system are expressed by Formula (8). Even in a case of the orthogonal coordinate system, the coordinates are first expressed on the polar coordinate system (t, θ, φ), and then can be calculated by arranging it at a new point (x', y', z') where the azimuth angle θ is k times and the z-axis direction is k times.

[Math. 3]

$$\begin{pmatrix} x' \\ y' \\ z' \end{pmatrix} = \begin{pmatrix} t'\cos\theta' \\ t'\sin\theta' \\ z' \end{pmatrix} = \begin{pmatrix} t\cos k\theta \\ t\sin k\theta \\ kz \end{pmatrix} \quad (8)$$

In Formula (8), in a case where the enlargement factor k is larger than 1, the image is enlarged, and in a case where the enlargement factor k is smaller than 1, the image is shrunk. In a case where the enlargement factor k is 1, there is no enlargement/reduction transformation and it matches the right side of Formula (1).

The orthogonal coordinate transformation unit 143 transforms the coordinates (t' cos θ', t' sin θ', z')=(t cos kθ, t sin kθ, kz) on the cylindrical coordinate system after scaling into the orthogonal coordinate system. The orthogonal coordinate transformation unit 143 supplies the five-element data of the coordinates (x', y', z') of each vertex of the spherical model and its corresponding texture coordinates (u, v), which are the vertex array data after the transformation, to the rendering unit 128.

As described above, in the case where the display image is enlarged or shrunk on the basis of the Zoom operation performed by the viewer/listener, the vertex data transformer 127 transforms the vertex array data of the five elements of the coordinates (x, y, Z) and the texture coordinates (u, v) into five-element vertex array data of the coordinates (x', y', z') and the texture coordinates (u, v), which correspond to the enlargement factor k, and supplies it to the rendering unit 128.

In other words, the rendering unit 128 is only sufficient to perform typical processing of generating a perspective projection image of the viewer/listener's field of view using the five-element vertex array data regardless of whether or not the display image is subjected to the enlargement/reduction, and it may not necessarily change the rendering processing depending on whether or not the display image is subjected to the enlargement/reduction.

As illustrated in FIG. 8, only the coordinates (x, y, z) are transformed by the scaling processing, but the texture coordinates (u, v) are not changed. Thus, the mapping unit 123 also may not necessarily change the processing depending on whether the display image is subjected to the enlargement/reduction.

Figure 11:
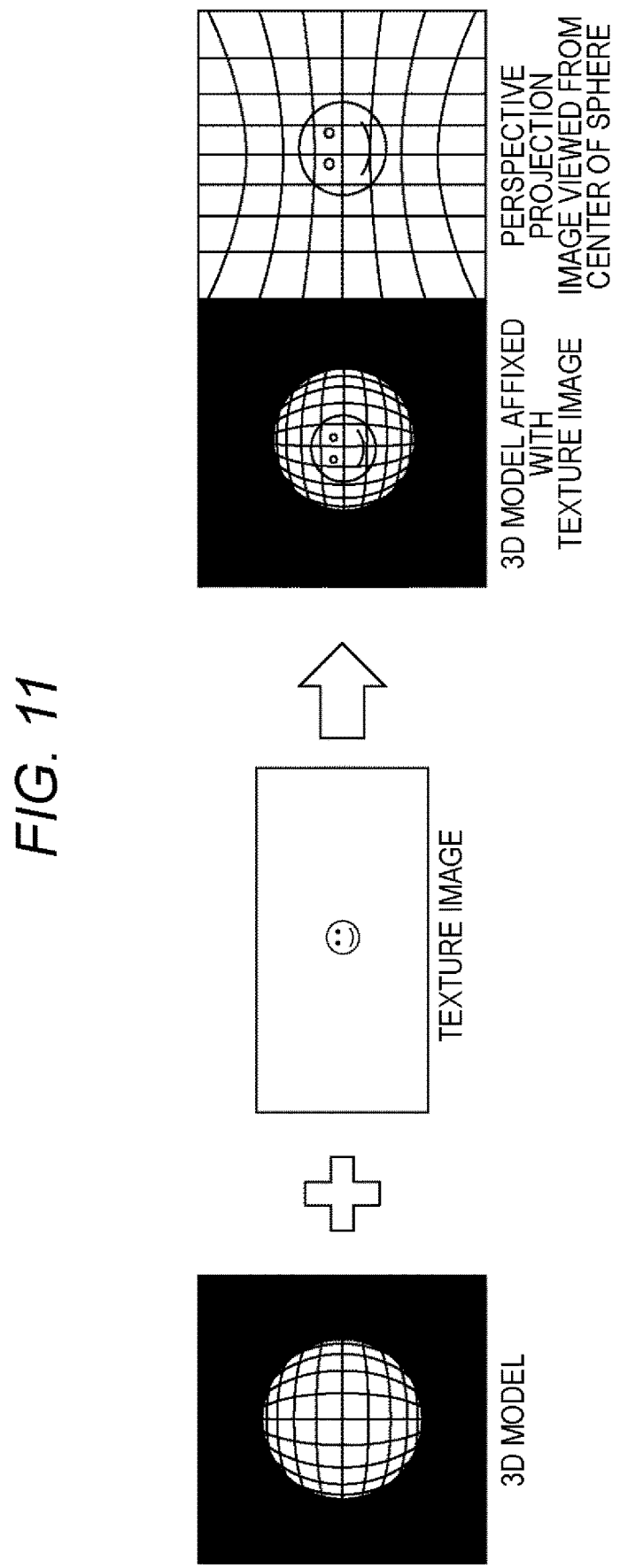
FIG. 11 is a conceptual diagram of a 3D model image and a perspective projection image in a case where scaling processing is not performed.
Figure 12:
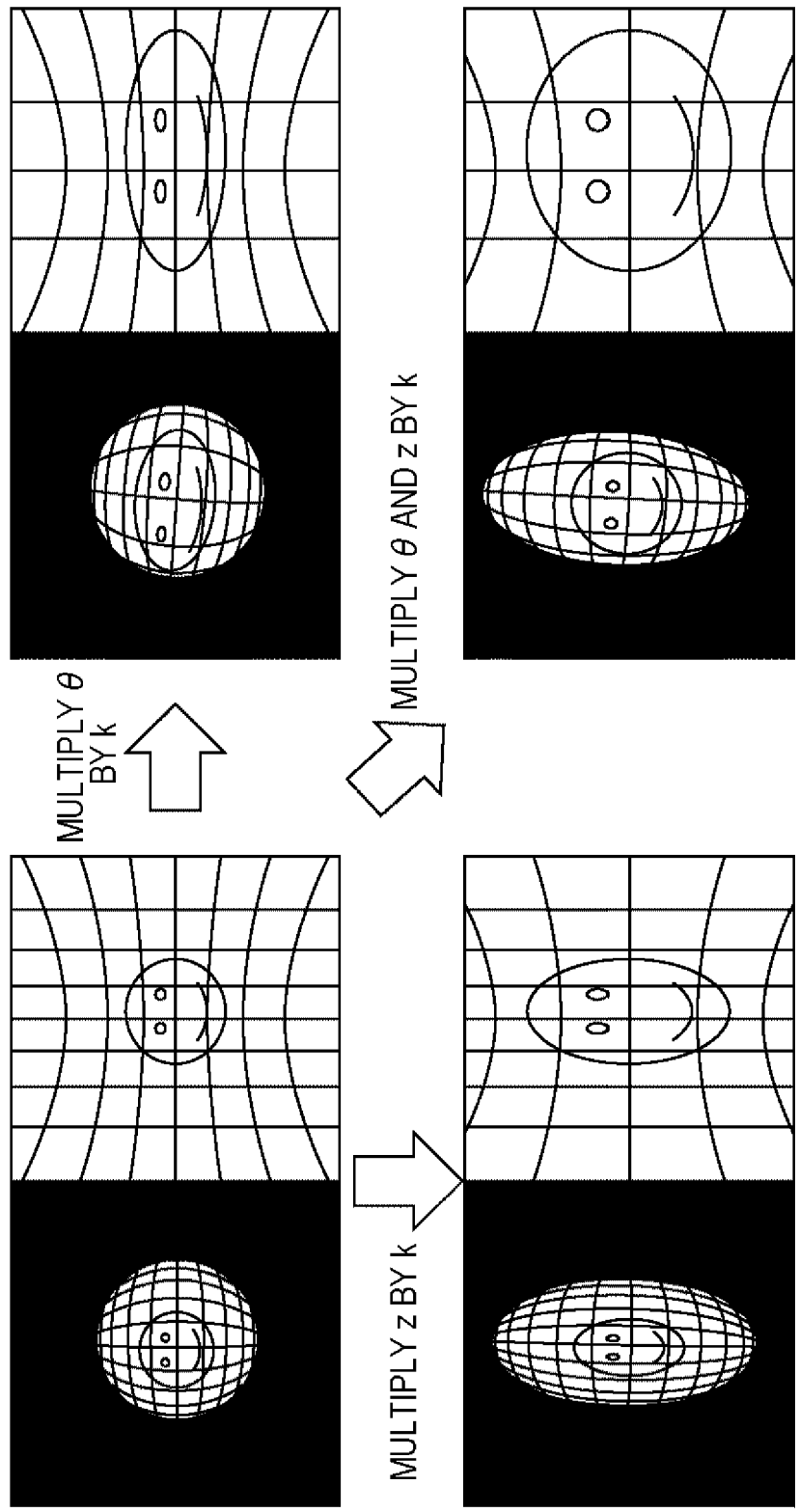
FIG. 12 is a conceptual diagram of a 3D model image and a perspective projection image in a case where scaling processing is performed.

FIGS. 11 and 12 are conceptual diagrams of a perspective projection image of a 3D model image obtained by affixing a texture image of equirectangular mapping to a spherical 3D model as viewed from the center of the sphere.

FIG. 11 is an example of a 3D model image and a perspective projection image in a case where scaling processing is not performed.

On the other hand, FIG. 12 is a conceptual diagram illustrating a processing result obtained by performing enlargement processing (k>1) on the 3D model image and the perspective projection image illustrated in FIG. 11 with respect to the azimuth angle θ, the vertical direction z, and both of them.

As illustrated in the upper right of FIG. 12, in the processing of multiplying the azimuth angle θ by k as Formula (6), the radius of the unit sphere remains as it is, but the texture image is affixed to the spherical surface while being stretched horizontally.

As illustrated in the lower left of FIG. 12, in the processing of multiplying the vertical direction z by k as Formula (7), the spherical model is stretched vertically as a whole and the perspective projection image is also stretched vertically.

As illustrated in the lower right of FIG. 12, in the processing of multiplying both the azimuth angle θ and the vertical direction z by k, the texture image is stretched both horizontally and vertically, and finally, an enlarged image having an aspect ratio of 1:1 is obtained.

However, the aspect ratio of 1:1 is a perspective projection image in a case where the line-of-sight direction is oriented in the horizontal direction and its vicinity. In a case where the line-of-sight direction is oriented in the upward or downward direction, it is necessary to pay attention that the perspective projection image is shrunk by the extent that the spherical surface of the 3D model extends in the z-axis direction and is farther than the original distance, and so deformation due to scaling of the azimuth angle θ is visible. This scaling processing is processing for enlarging or reducing a perspective projection image mainly in the horizontal direction.

In the enlarged image in which both the azimuth angle θ and the vertical direction z are multiplied by k by the mapping transformation $f_k$, others than the vertical direction are a natural enlarged image as in the perspective projection image at the lower right of FIG. 12. In addition, even after performing the mapping transformation $f_k$, only a static 3D model in which the coordinates (x, y, z) before performing the scaling processing are moved to the newly obtained coordinates (x', y', z') is rendered, which prevents unexpected deformation or movement of the image caused by a change in the viewing/listening direction due to looking around from occurring. This makes it possible to be less likely to occur VR motion sickness caused by an enlargement or the like due to a simple change in the field of view.

Further, the VR motion sickness also occurs when the horizon line is tilted or when an object that originally extends in the vertical direction looks oblique. In Formula (8), the θ component of the cylindrical coordinate system corresponds to the x-y component of the orthogonal coordinate system but the z component does not depend on the x-y component, so the mapping transformation $f_k$ does not cause the case where the horizon line is tilted or the perpendicular object is inclined. Such characteristics are also factors in the present technology that make it difficult for VR motion sickness to occur.

(Rendering Method of Scaled Image)

This technique performs scaling of the rendered image (3D model image) by scaling the azimuth angle θ and vertical direction z of the cylindrical coordinate system. The range of values of the azimuth angle θ is $-\pi<=\theta<=\pi$ before the scaling and then it is $-k\pi<=\theta<=k\pi$, which exceeds 360 degrees that can be rendered in the case of enlargement and is less than 360 degrees in the case of reduction. Thus, it is necessary to cope with the case where the rendered image exceeds 360 degrees and with the case where it is less than 360 degrees due to the scaling.

Thus, in the case where the omnidirectional image is enlarged by k times, the scaling unit 142 performs first enlargement processing of cropping an image exceeding 360 degrees or second enlargement processing for rendering so that one circling round of the original image (scenery) can be seen in a case where the viewer/listener rotates k revolutions horizontally.

In the first enlargement processing of cropping an image exceeding 360 degrees, the scaling unit 142 performs processing of deleting the data satisfying $\theta'<-\pi$ and the data satisfying $\pi<\theta'$ from the vertex array data of the coordinates (x', y', z') and the texture coordinates (u, v) obtained by applying the enlargement factor k.

Figure 13:
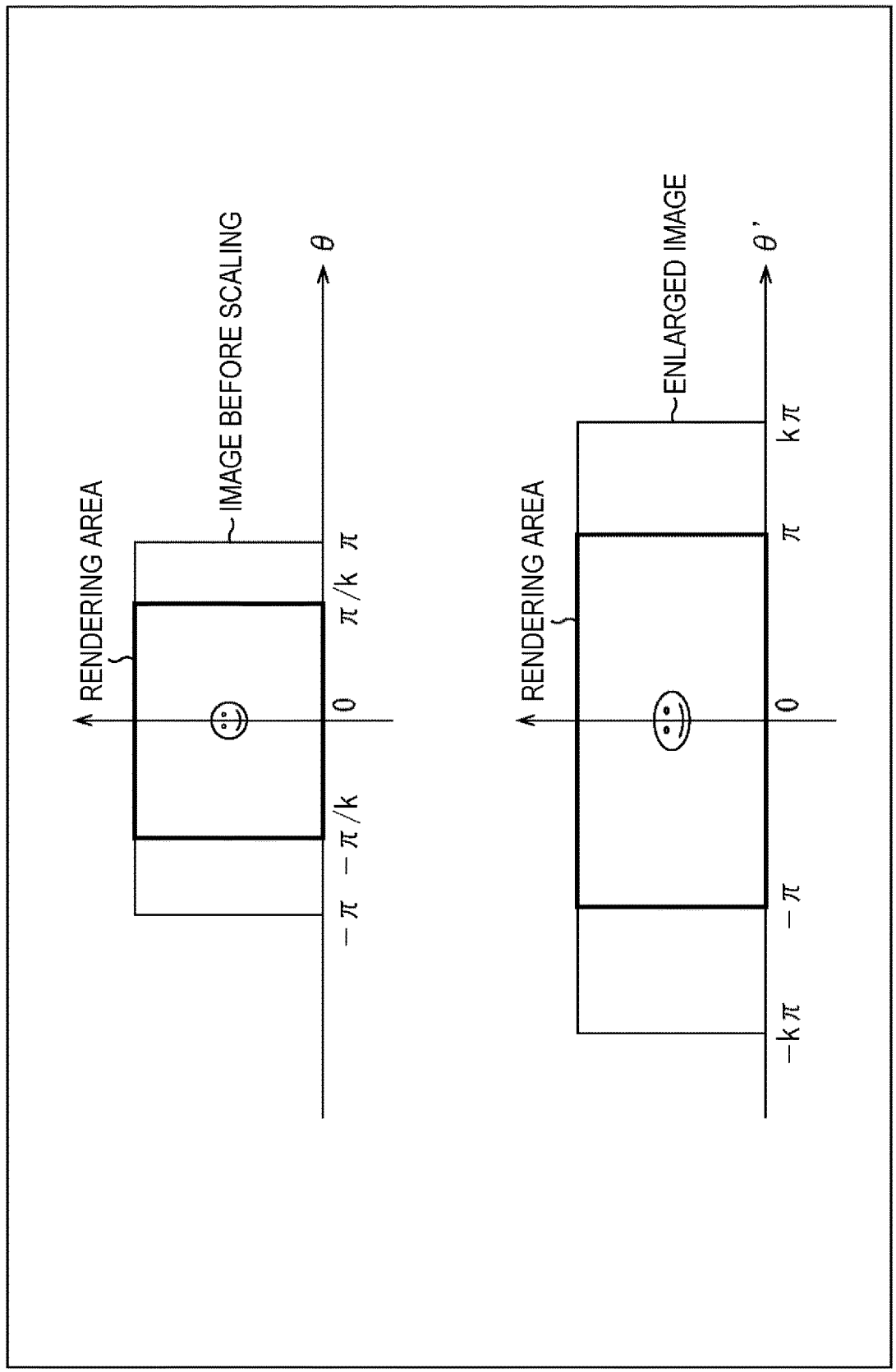
FIG. 13 is a conceptual diagram of first enlargement processing.

FIG. 13 is a schematic diagram illustrating an area rendered in the first enlargement processing.

In the first enlargement processing, the image in the range of $(-\pi/k)<=\theta<=(\pi/k)$ before scaling is assigned to the range of $-\pi<=\theta<=\pi$. The data of the area satisfying $\theta'<-\pi$ of the enlarged image and the data of the area satisfying $\pi<\theta'$ of the enlarged image are deleted from the vertex array data.

Figure 14:
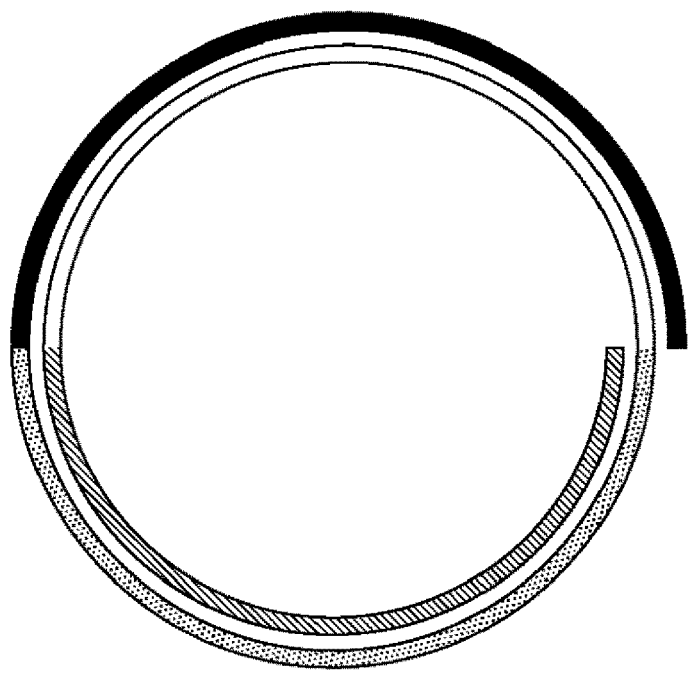
FIG. 14 is a conceptual diagram of second enlargement processing.
Figure 14:
Figure 14:
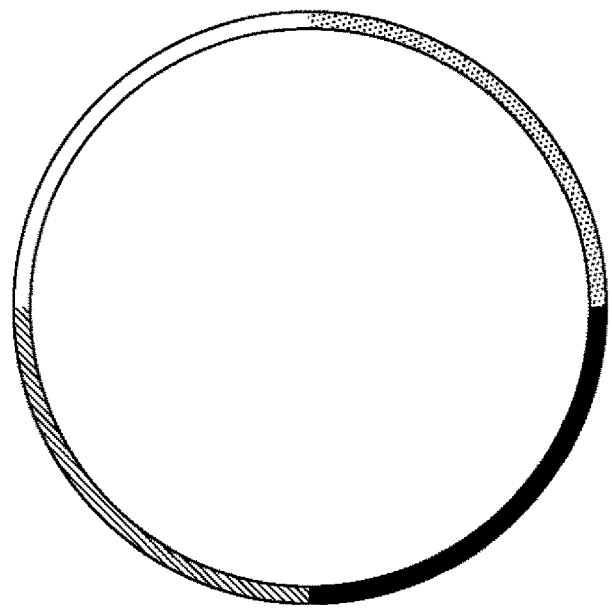

FIG. 14 is a conceptual diagram of the second enlargement processing in the case of k=2.

In the second enlargement processing in the case of k=2, one circling round of the original scenery is to be seen during the viewer/listener rotates two revolutions. In a case where the viewer/listener moves the line-of-sight direction to the left or right while viewing the rendered image being enlarged, it is possible to determine which part of the overlapping data is to be displayed by adding a constraint that the rendered image necessitates to be displayed continuously on the left and right direction.

In order to add the constraint that the rendered image necessitates to be displayed continuously on the left and right direction, a horizontal angle of the continuously changing line of sight direction is defined. The typical range of the horizontal angle is from $-\pi$ to $\pi$, and if it exceeds a range directly behind, it changes discontinuously between $-\pi$ and $\pi$, but the horizontal angle $\xi$ is a horizontal angle defined such that the clockwise rotation is monotonically increasing and the counterclockwise rotation is monotonically decreasing so as to change continuously in a normal condition. The range of the horizontal angle $\xi$ is $-\infty<=\xi<=\infty$.

Figure 15:
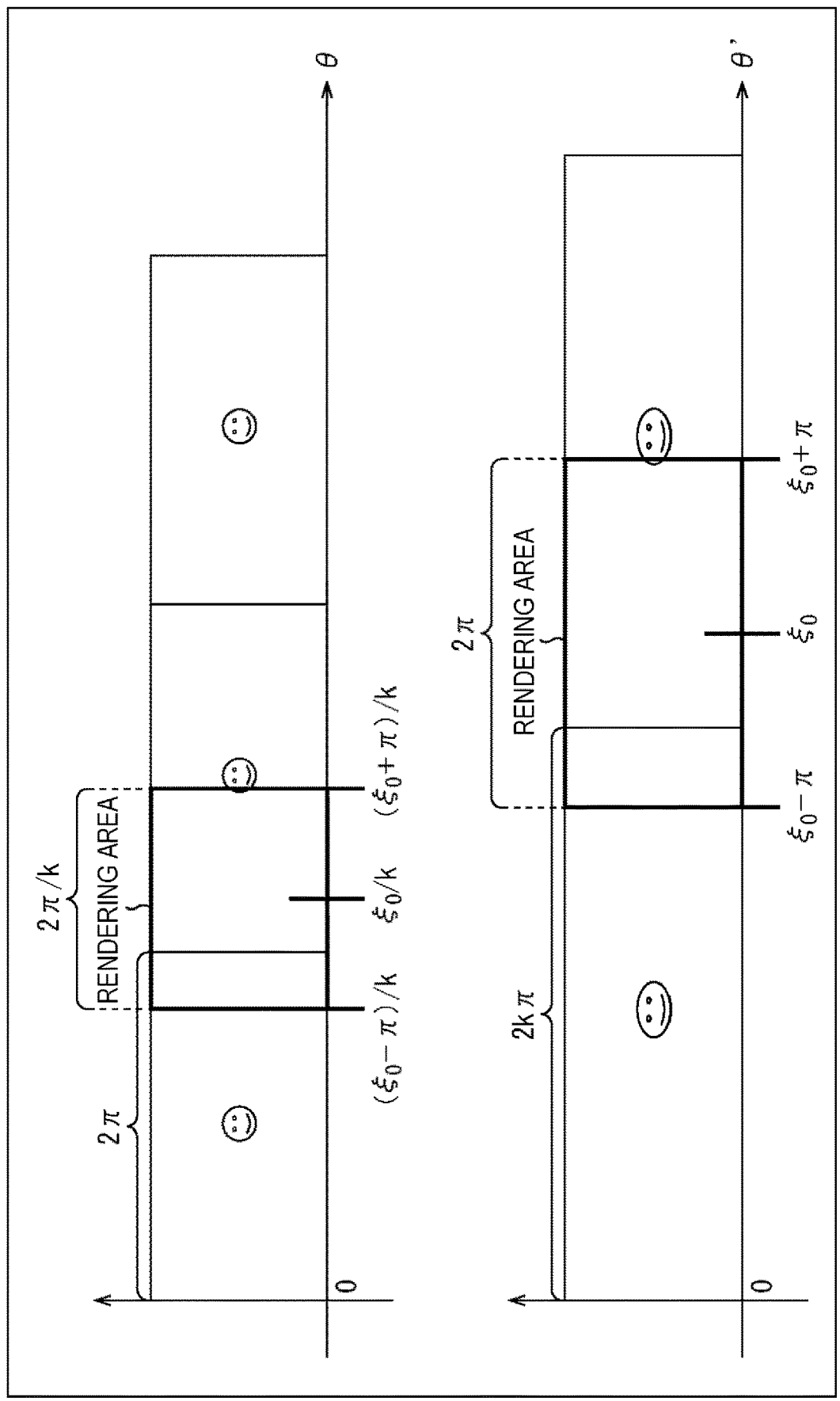
FIG. 15 is a diagram illustrated to describe second enlargement processing.

FIG. 15 is a schematic diagram illustrating a rendering area in a case where a viewer/listener is looking at a k-times enlarged image toward the direction satisfying the horizontal angle $\xi=\xi_0$.

In the case where the mapping transformation $f_k$ is performed upon the enlargement, an overlapping portion occurs in the 3D space, so the scaling unit 142 performs the determination on the basis of the azimuth angle $\theta$ before the enlargement.

The range of $(\xi_0-\pi)/k<\theta<(\xi_0+\pi)/k$ is the rendering area, so the scaling unit 142 deletes the vertex array data in the other ranges and then performs the mapping transformation $f_k$ upon the enlargement to create vertex data. By doing so, the range of the vertex array data after the transformation is exactly from $-\pi$ to $\pi$ to cover the entire celestial range.

On the other hand, in a case where the omnidirectional image is shrunk by a factor of 1/k, the scaling unit 142 repeatedly performs rendering of the shrunk image so that the rendered image is not interrupted. In this case, circling round k times of the original image (scenery) can be seen in the case where the viewer/listener rotates one revolution horizontally.

Moreover, a black image can be embedded as an image of a portion less than 360 degrees upon the reducing processing, instead of using the omnidirectional image shrunk to a factor of 1/k.

(Processing in Generation Apparatus)

Figure 16:
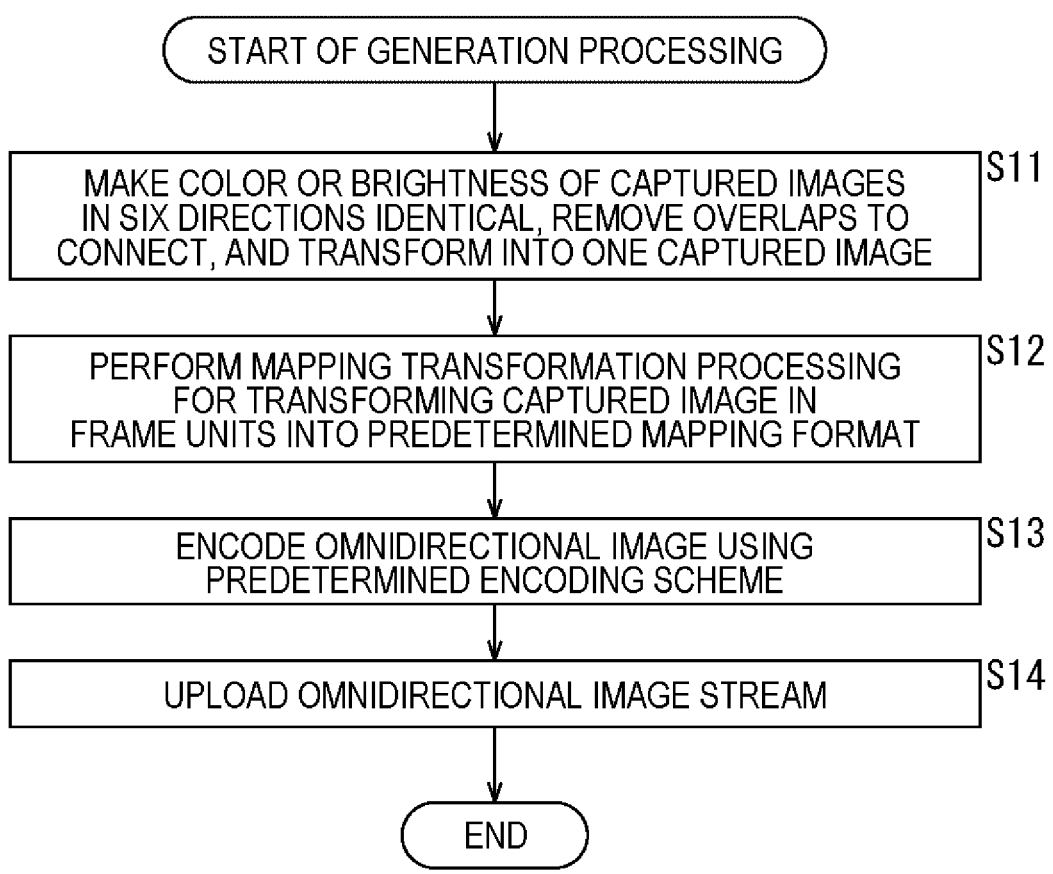
FIG. 16 is a flowchart illustrated to describe generation processing according to the first embodiment.

FIG. 16 is a flowchart illustrated to describe generation processing performed by the generation apparatus 12 in FIG. 1. This processing is started, in one example, when moving images in six directions captured by the six cameras 11A-1 to 11A-6 of the imaging apparatus 11 are supplied.

In step S11 as the first step, the stitching unit 21 makes colors or brightness of the captured images in the six directions supplied from the respective cameras 11A identical for each frame, removes overlaps to connect, and then transforms them into a single captured image. The stitching unit 21 generates, in one example, an equirectangular image as one captured image, and supplies the equirectangular image in frame units to the mapping transformer 22.

In step S12, the mapping transformer 22 performs mapping transformation processing on the captured image (e.g., an equirectangular image) in frame units supplied from the stitching unit 21 into a mapping format for mapping to a predetermined 3D model.

In one example, in a case where the delivery server 13 delivers an omnidirectional image using a cubic model as a 3D model, the mapping transformer 22 transforms the omnidirectional image of equirectangular mapping supplied from the stitching unit 21 into the omnidirectional image of cube mapping. In a case where the mapping format of the omnidirectional image supplied from the stitching unit 21 is the same as the mapping format supplied to the delivery server 13, the mapping transformation processing is unnecessary, and the omnidirectional image supplied from the stitching unit 21 is supplied to the encoder 23 without transformation.

In step S13, the encoder 23 encodes the omnidirectional image supplied from the mapping transformer 22 using a predetermined encoding scheme such as the MPEG-2 or AVC standard to generate an encoded stream. The encoder 23 supplies the generated encoded stream of the omnidirectional image to the transmitter 24.

In step S14, the transmitter 24 uploads the omnidirectional image streams supplied from the encoder 23 to the delivery server 13 and then the processing ends.

(Description of Processing in Playback Apparatus)

Figure 17:
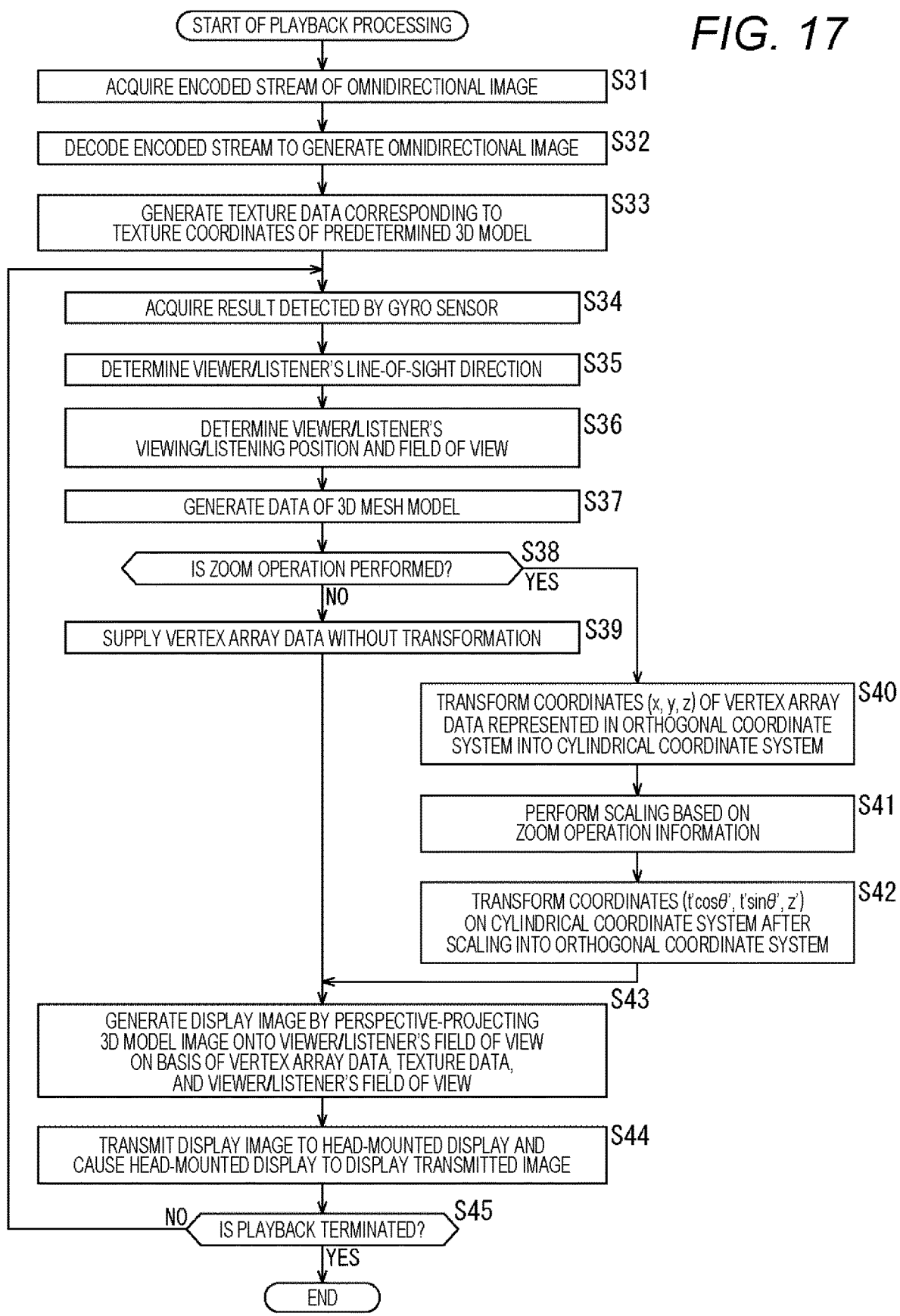
FIG. 17 is a flowchart illustrated to describe playback processing according to the first embodiment.

FIG. 17 is a flowchart illustrated to describe playback processing performed by the playback apparatus 15 in FIG. 1. This playback processing is started, in one example, when the playback apparatus 15 detects a power-on or a processing start operation.

In step S31, as the first step, the transceiver 121 requests the omnidirectional image from the delivery server 13 via the network 14 and acquires the encoded stream of the omnidirectional image transmitted from the transceiver 103 of the delivery server 13 in response to the request. The transceiver 121 supplies the obtained encoded stream of the omnidirectional image to the decoder 122.

In step S32, the decoder 122 decodes the encoded stream supplied from the transceiver 121 to generate an omnidirectional image. The decoder 122 supplies the generated omnidirectional image to the mapping unit 123.

In step S33, the mapping unit 123 generates texture data (R, G, B) corresponding to the texture coordinates (u, v) of a predetermined 3D model using the omnidirectional image supplied from the decoder 122. The mapping unit 123 supplies the generated texture data to the rendering unit 128 by storing the generated texture data in a texture buffer accessible by the rendering unit 128.

In step S34, the acquisition unit 124 acquires the detection result of the gyro sensor 16B in FIG. 1 from the head-mounted display 16 and supplies the result to the line-of-sight detector 125.

In step S35, the line-of-sight detector 125 determines a viewer/listener's line-of-sight direction in the coordinate system of the 3D model on the basis of the detection result of the gyro sensor 16B that is supplied from the acquisition unit 124.

In step S36, the line-of-sight detector 125 determines the viewer/listener's viewing/listening position and field of view in the coordinate system of the 3D model and supplies them to the rendering unit 128. More specifically, the line-of-sight detector 125 acquires a captured image of the marker 16A from the camera 15A and detects a viewing/listening position in the coordinate system of the 3D model on the basis of the captured image. Then, the line-of-sight detector 125 determines the viewer/listener's field of view in the 3D model coordinate system on the basis of the detected viewing/listening position and line-of-sight direction and supplies it to the rendering unit 128.

In step S37, the 3D model generation unit 126 generates data of a 3D mesh model in a virtual 3D space and supplies the data to the vertex data transformer 127. This data of the 3D mesh model includes vertex array data constituted by five elements of the coordinates (x, y, z) of each vertex of the 3D model and the corresponding texture coordinates (u, v) as illustrated in FIG. 7.

In step S38, the vertex data transformer 127 determines whether the viewer/listener performs a zoom operation on the basis of the zoom operation information supplied from the acquisition unit 124. In one example, in the case where the viewer/listener performs the zoom operation on the controller 16C, the zoom operation information associated with the zoom operation is supplied to the acquisition unit 124 and then is supplied from the acquisition unit 124 to the vertex data transformer 127.

If it is determined in step S38 that the zoom operation is not performed, the processing proceeds to step S39, in which the vertex data transformer 127 supplies the vertex array data supplied from the 3D model generation unit 126 to the rendering unit 128 without transformation. In other words, the vertex array data obtained by subjecting the vertex array data supplied from the 3D model generation unit 126 to the mapping transformation $f_k$ of Formula (8) with the enlargement factor k being 1 is supplied to the rendering unit 128.

On the other hand, if it is determined in step S38 that the zoom operation is performed, the processing proceeds to step S40, in which the vertex data transformer 127 executes the vertex data transformation processing including steps S40 to S42.

In step S40 as the first step of the vertex data transformation processing, the cylindrical coordinate transformation unit 141 transforms the coordinates (x, y, z) of the vertex array data represented in the orthogonal coordinate system into the coordinates (t, θ, z) on the cylindrical coordinate system on the basis of the correspondence relationship expressed by Formula (1).

In step S41, the scaling unit 142 performs the scaling based on the zoom operation information by performing the mapping transformation $f_k$ that multiplies the coordinates (t, θ, z) transformed on the cylindrical coordinate system by k. Specifically, the scaling unit 142 performs the mapping transformation $f_k$ represented by Formulas (5) to (7).

In step S42, the orthogonal coordinate transformation unit 143 transforms the coordinates (t' cos θ', t' sin θ', z') on the cylindrical coordinate system after the scaling into the orthogonal coordinate system. Then, the vertex array data constituted by the five elements of the coordinates (x', y', z') of each vertex of the 3D mesh model transformed into the orthogonal coordinate system and the corresponding texture coordinates (u, v) is supplied to in the rendering unit 128.

In step S43, the rendering unit 128 generates a display image by perspective-projecting the 3D model image onto the viewer/listener's field of view on the basis of the vertex array data supplied from the vertex data transformer 127 (the orthogonal coordinate transformation unit 143 thereof), the texture data (R, G, B) supplied from the mapping unit 123, and the viewer/listener's field of view supplied from the line-of-sight detector 125.

In step S44, the rendering unit 128 transmits the display image to the head-mounted display 16, which is caused to display it.

In step S45, the playback apparatus 15 determines whether to terminate the playback. In one example, in a case where the viewer/listener performs an operation to terminate the playback, the playback apparatus 15 determines to terminate the playback.

If it is determined in step S45 that the playback is not to be terminated, the processing returns to step S34, and the processing of steps S34 to S45 described above is repeated. On the other hand, if it is determined in step S45 that the playback is to be terminated, the playback processing ends.

(Modification of Playback Apparatus)

Figure 18:
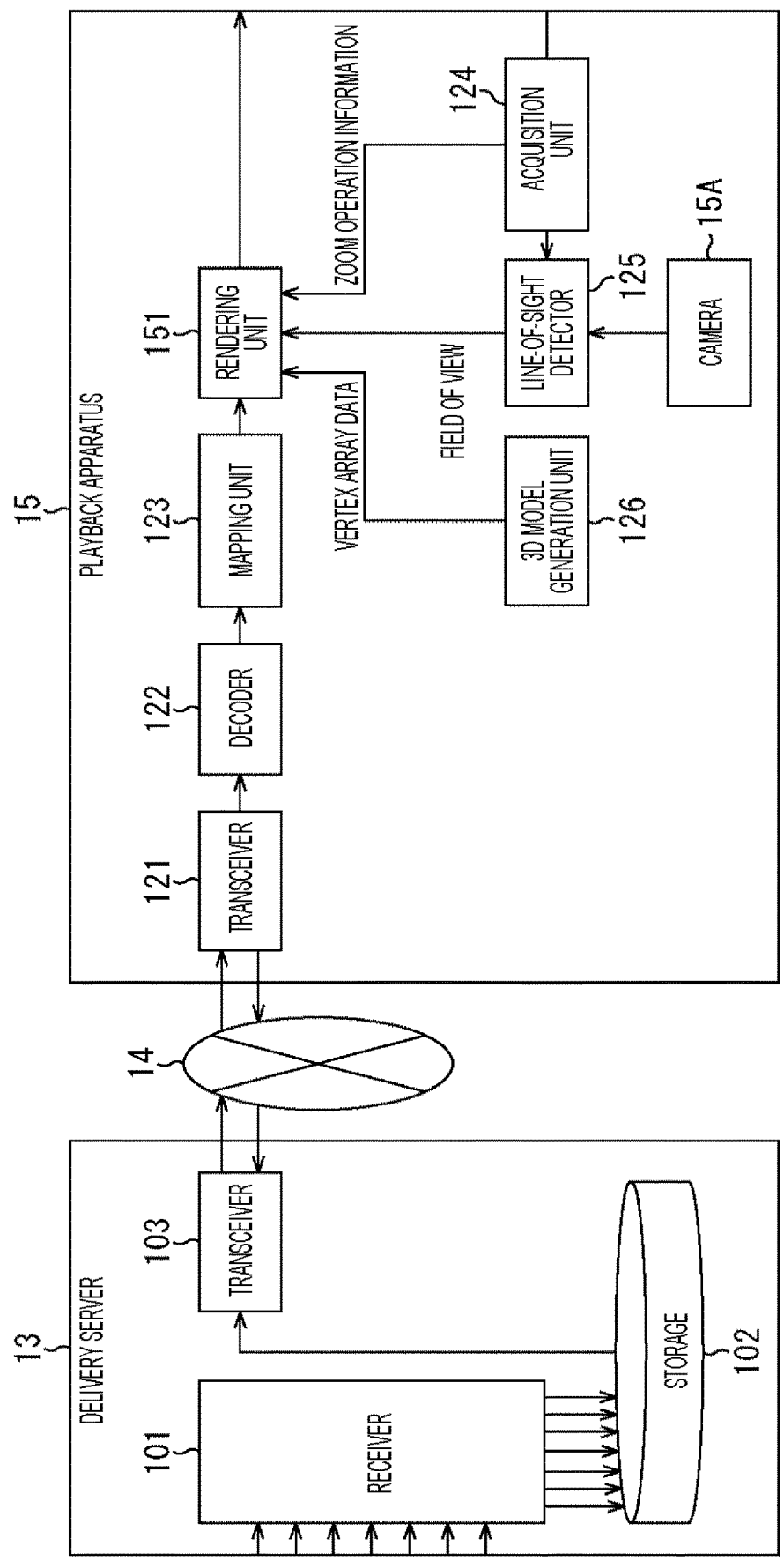
FIG. 18 is a block diagram illustrating a modification of the playback apparatus.

FIG. 18 is a block diagram illustrating a modification of the playback apparatus 15.

FIG. 18 is a block diagram corresponding to FIG. 4, and also shows the configuration of the delivery server 13, but in FIG. 18, only the configuration of the playback apparatus 15 is different.

The exemplary configuration of the playback apparatus 15 illustrated in FIG. 18 is an exemplary configuration that is employable in the case where the mapping format of the omnidirectional image is the equirectangular mapping.

Comparing FIG. 18 with FIG. 4, the playback apparatus 15 illustrated in FIG. 18 includes the rendering unit 151, while the playback apparatus 15 illustrated in FIG. 4 includes the rendering unit 128. In addition, in FIG. 18, the vertex data transformer 127 is not included, so the vertex array data output from the 3D model generation unit 126 is directly supplied to the rendering unit 151. Further, the zoom operation information is supplied from the acquisition unit 124 to the rendering unit 151. The rendering unit 151 differs from the rendering unit 128 in FIG. 4 in that predetermined processing based on the zoom operation information is performed. Other components in the playback apparatus 15 of FIG. 18 are similar to those in the playback apparatus 15 of FIG. 4.

In the playback apparatus 15 of FIG. 18, the vertex data transformer 127 is not included, so the mapping transformation $f_k$ is not performed, that is, the normal vertex array data is supplied to the rendering unit 151, regardless of whether or not the viewer/listener performs the zoom operation.

The rendering unit 151 changes the scale of the three-dimensional orthogonal space coordinates (x, y, z) and the texture coordinates (u, v) on the basis of the zoom operation information supplied from the acquisition unit 124. In typical 3D rendering software, the API is provided to change the scale of each of three-dimensional orthogonal space coordinates (x, y, z) and texture coordinates (u, v), and simple enlargement/reduction can be performed without rewriting vertex data or texture data. In one example, in OpenGL, the scales of both x, y, z and u, v can be changed using the "glScale" function.

As illustrated in FIG. 5, the horizontal axis of the equirectangular projection texture is parallel to the azimuth angle θ of the cylindrical coordinates. Thus, the mapping of θ'=kθ in Formula (5) is capable of being processed only by scaling the u-axis.

Figure 19:
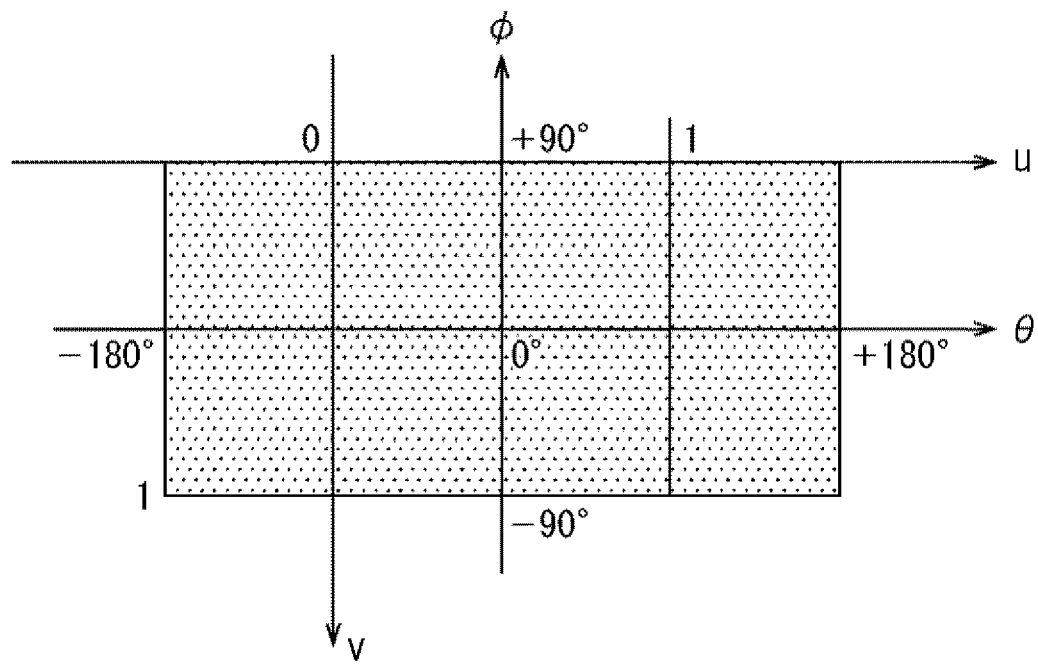
FIG. 19 is a conceptual diagram of texture data obtained by re-scaling the u-axis.

FIG. 19 illustrates a conceptual diagram of texture data obtained by re-scaling the u-axis.

The difference between the texture data of FIG. 5 and the texture data of FIG. 19 is that the position of (0, 1) on the u-axis is changed. Thus, by changing the scale of the u-axis, even if both the texture data has the same (u, v), it is possible to access a position obtained by multiplying θ by k with respect to the texture data of FIG. 5.

Similarly, the scaling of the z-axis of the three-dimensional orthogonal space coordinates (x, y, z) makes it possible to perform the mapping of z'=kz in Formula (7).

In other words, the rendering unit 151 performs the mapping transformation $f_k$ by a combination of the scale change of the z-axis of the three-dimensional orthogonal space coordinates (x, y, z) and the scale change of the u-axis of the texture coordinates (u, v) on the basis of the zoom operation information.

As illustrated in FIG. 8, the processing of replacing all the coordinates (x, y, z) of the vertex array data with the coordinates (x', y', z') subjected to the mapping transformation necessitates the processing and rewriting of a large amount of data.

However, in a case where the mapping format of the omnidirectional image is the equirectangular mapping, by supplying the vertex array data that is not subjected to the enlargement/reduction to the rendering unit 151 and changing the scale of the rendering unit 151 as in the normal case with no use of the vertex data transformer 127 as described above, it is possible to achieve enlargement/reduction display in response to the viewer/listener's zoom operation. This makes it possible to more easily implement the enlargement/reduction display in response to the zoom operation, which generally enables high-speed operation with a small amount of code.

2. Second Embodiment (Exemplary Configuration of Delivery System According to Second Embodiment)

Next, a description is given of the delivery system of a second embodiment to which the technology of the present disclosure is applied.

The overall configuration of the delivery system 10 according to the second embodiment is similar to that of FIG. 1, so illustration thereof is omitted.

In the case where the above-described omnidirectional image enlargement processing is performed, the resolution in the direction being viewed is necessary and the range within the field of view of the head-mounted display 16 is narrowed, so the direction opposite to the direction being viewed is difficult to be included in the field of view.

Thus, the viewport dependent projection mapping scheme that uses mapping with increased resolution in a particular direction is available. The viewport dependent projection mapping is a scheme of using projection mapping having the biased pixel density to increase the resolution in a particular direction and performing playback while switching the data of the projection mapping having different high-resolution directions depending on the viewing/listening direction. The viewport dependent projection mapping is disclosed in the chapter "A.3.2.5 Truncated pyramid" of Working Draft "WD on ISO/IEC 23000-20 Omnidirectional Media Application Format" published at the Geneva meeting in June 2016 of the MPEG meeting. In this scheme, the number of pixels assigned to the front area is large and the resolution is high. A plurality of bitstreams with various front directions is prepared, and the bitstreams are reproduced while being switched depending on the direction in which the viewer/listener is facing.

In the second embodiment of the delivery system described below, a configuration is employed in which a plurality of directions for increasing the resolution is set for a range of 360 degrees in the horizontal direction that the viewer/listener looks around as in the viewport dependent projection mapping and the playback is performed while a plurality of prepared bitstreams is switched depending on the direction in which the viewer/listener is facing.

Figure 20:
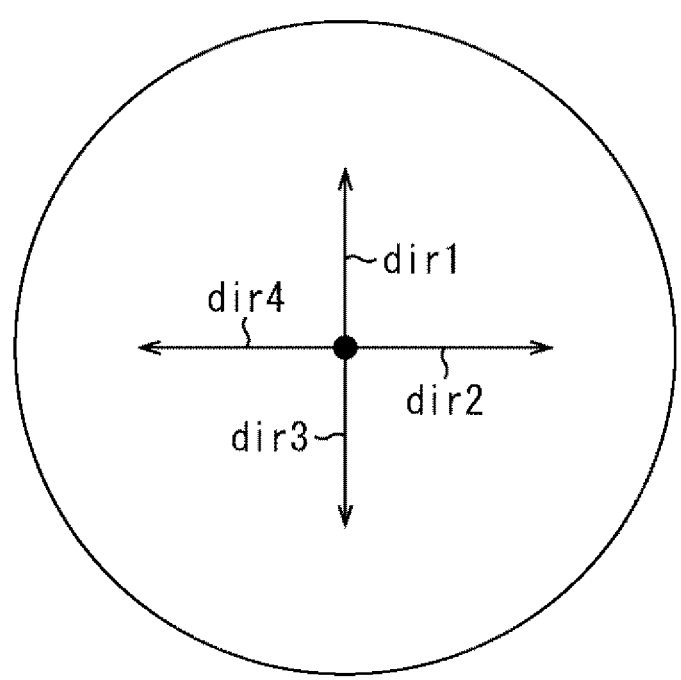
FIG. 20 is a diagram illustrated to describe a high-resolution direction in a delivery system according to a second embodiment.

Specifically, as illustrated in FIG. 20, as viewing the spherical surface as a 3D model from above, four directions dir1 to dir4 are set horizontally from the center of the sphere as directions for increasing the resolution, and the description is given of a case of performing the playback while switching between five encoded streams having four encoded streams corresponding to four directions dir1 to dir4 and one encoded stream having uniform resolution in all directions, which is used in the case of no enlargement operation.

Figure 21:
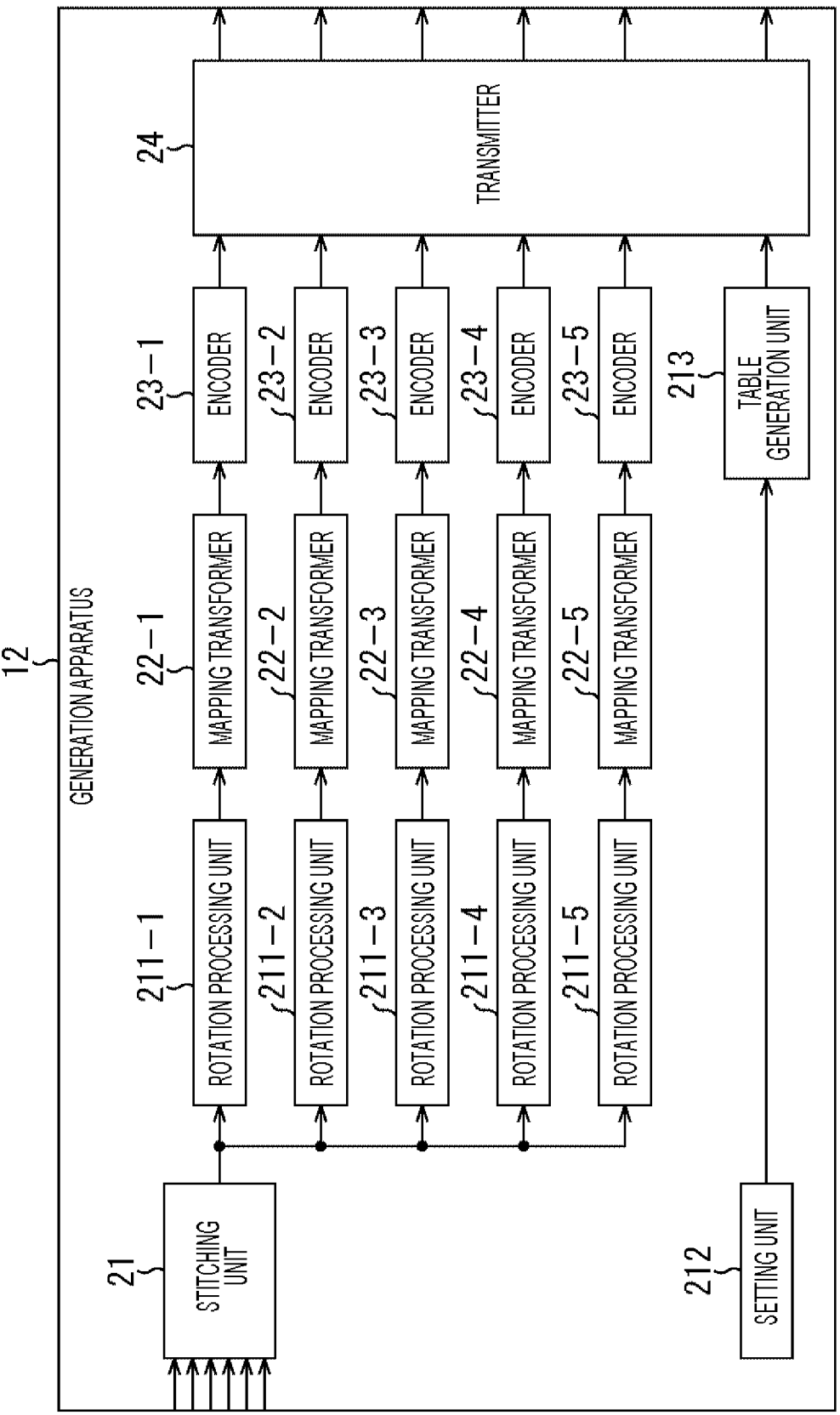
FIG. 21 is a block diagram illustrating an exemplary configuration of a generation apparatus according to the second embodiment.

FIG. 21 is a block diagram illustrating an exemplary configuration of the generation apparatus 12 of the delivery system 10 according to the second embodiment.

The generation apparatus 12 in FIG. 21 includes a stitching unit 21, mapping transformers 22-1 to 22-5, encoders 23-1 to 23-5, a transmitter 24, rotation processing units 211-1 to 211-5, a setting unit 212, and a table generation unit 213.

In FIG. 21, the same reference numerals are given to the portions corresponding to the generation apparatus 12 in FIG. 3, so the description of the portions will be appropriately omitted.

In the generation apparatus 12 of FIG. 21, the rotation processing unit 211 is additionally included between the stitching unit 21 and the mapping transformer 22 in the generation apparatus 12 of FIG. 3, and a set of five rotation processing units 211, a set of five mapping transformers 22, and a set of five encoders 23 are provided. The number (five) of each set of the rotation processing units 211, the mapping transformers 22, and the encoders 23 corresponds to five encoded streams including four encoded streams in which the four directions dir1 to dir4 in FIG. 20 have high-resolution directions and one encoded stream of uniform resolution.

The stitching unit 21 supplies the generated one captured image to the rotation processing units 211-1 to 211-5.

The rotation processing units 211-1 to 211-5 rotate (shift) the captured image (e.g., equirectangular images) supplied from the stitching unit 21 in frame units around the center of the image such that the center of the image is in the high-resolution direction. The setting unit 212 instructs which direction is the high-resolution direction. The rotation processing units 211-1 to 211-5 differ only in the direction specified by the setting unit 212.

The mapping transformers 22-1 to 22-5 perform mapping of the captured images supplied from the rotation processing units 211-1 to 211-5, respectively, to a predetermined mapping format using the enlargement factor k supplied from the setting unit 212, and so generate an omnidirectional image in which the pixel at the center of the image is transformed to a high resolution by the enlargement factor k. In the generated omnidirectional image, the resolution in the direction opposite (right behind) the center of the image is low.

Figure 22:
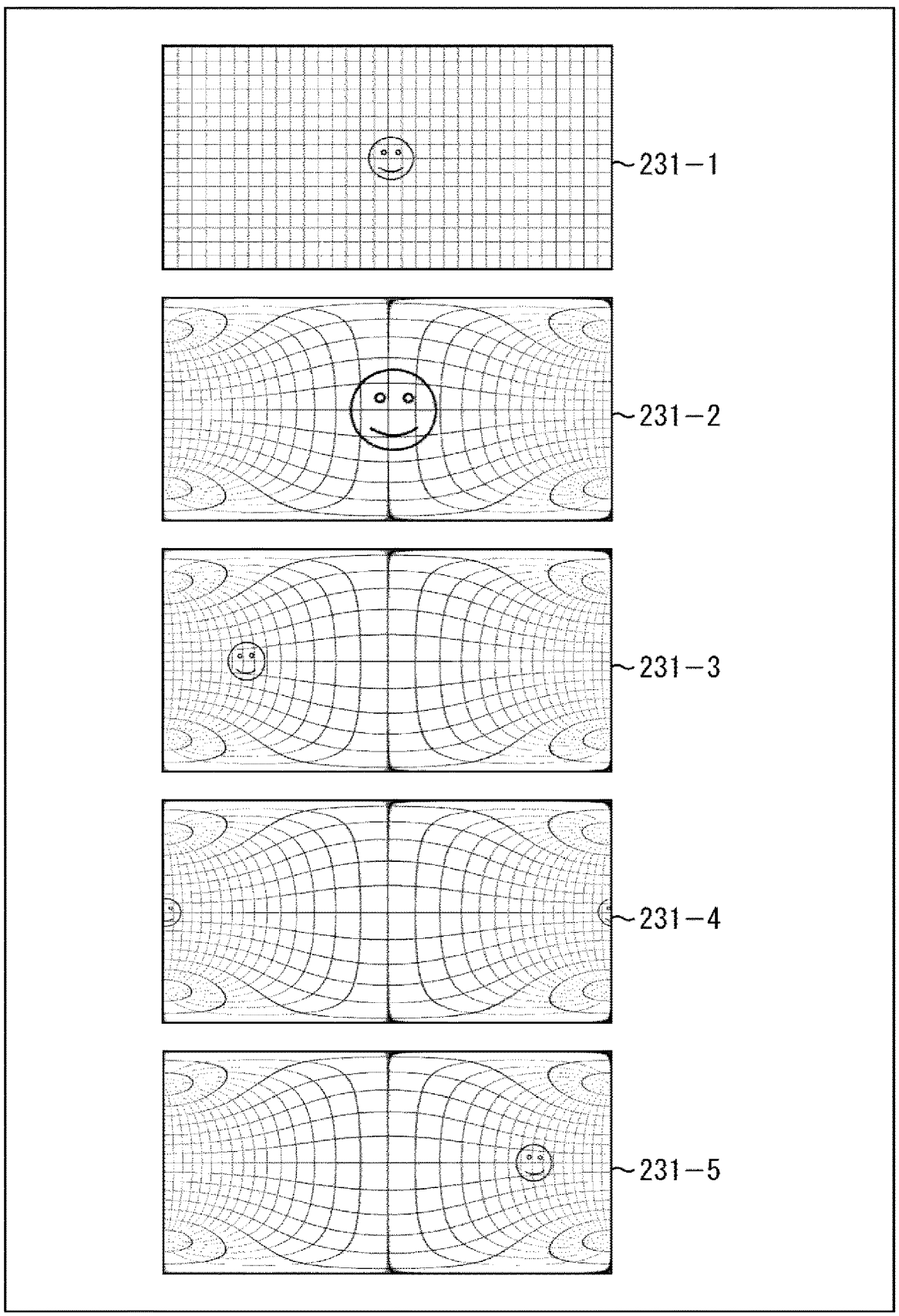
FIG. 22 is a conceptual diagram of five omnidirectional images in different high-resolution directions.

FIG. 22 is a conceptual diagram of five omnidirectional images generated by the mapping transformers 22-1 to 22-5.

The omnidirectional image 231-1 is an image that is subjected to the processing performed by the mapping transformer 22-1, and is an equirectangular image having a uniform resolution in all directions around 360 degrees in the horizontal direction. The center of the omnidirectional image 231-1 coincides with the direction dir1 in FIG. 20.

The omnidirectional image 231-2 is an image that is subjected to the processing performed by the mapping transformer 22-2, and is an equirectangular image transformed so that the direction dir1 in FIG. 20 has a high resolution out of 360 degrees in the horizontal direction.

The omnidirectional image 231-3 is an image that is subjected to the processing performed by the mapping transformer 22-3, and is an equirectangular image transformed so that the direction dir2 in FIG. 20 has a high resolution out of 360 degrees in the horizontal direction.

The omnidirectional image 231-4 is an image that is subjected to the processing performed by the mapping transformer 22-4, and is an equirectangular image transformed so that the direction dir3 in FIG. 20 has a high resolution out of 360 degrees in the horizontal direction.

The omnidirectional image 231-5 is an image that is subjected to the processing performed by the mapping transformer 22-5, and is an equirectangular image transformed so that the direction dir4 in FIG. 20 has a high resolution out of 360 degrees in the horizontal direction.

In one example, in the omnidirectional image 231-2, the center of the image is enlarged while maintaining the same direction, the enlargement factor decreases as the distance from the center increases, and the rear portion is shrunk, as compared with the omnidirectional image 231-1 having a uniform resolution. In a case where the omnidirectional image 231-2 whose enlargement factor is operated is affixed as a texture to a spherical model so that it can be viewed as the original celestial sphere without distortion, a density difference occurs in the pixel, so an omnidirectional image having a high resolution in the direction dir1 is played back.

The encoders 23-1 to 23-5 encode the omnidirectional images supplied from the corresponding mapping transformers 22-1 to 22-5, respectively, using a predetermined encoding scheme such as the MPEG-2 or AVC standard, and generate encoded streams.

The transmitter 24 uploads (transmits) the encoded streams of the omnidirectional images supplied from the encoders 23-1 to 23-5 to the delivery server 13 in FIG. 1. In this event, the five encoded streams generated by the encoders 23-1 to 23-5 are dynamically switched and played back, so the sync points such as the head picture or IDR picture of the group of picture (GOP), in one example, are made the same between the five encoded streams generated by the encoders 23-1 to 23-5.

The setting unit 212 determines a high-resolution direction to be treated as a front direction by the five sets of each of the rotation processing units 211, the mapping transformers 22, and the encoders 23 provided in parallel with respect to 360 degrees around the horizontal direction. Specifically, the setting unit 212 determines four high-resolution directions of directions dir1 to dir4 in FIG. 20 and supplies them to the rotation processing units 211-1 to 211-5. In one example, the setting unit 212 supplies the direction dir1 to the rotation processing units 211-1 and 211-2, the direction dir2 to the rotation processing unit 211-3, the direction dir3 to the rotation processing unit 211-4, and the direction dir4 to the rotation processing unit 211-4.

In addition, the setting unit 212 determines an enlargement factor k indicating how high the resolution is in the high-resolution direction by comparing it with the case where the resolution is uniform in all directions of 360 degrees around the horizontal direction, and supplies it to the mapping transformers 22-1 to 22-5. In one example, the setting unit 212 supplies an enlargement factor k=1.0 to the mapping transformer 22-1, and supplies an enlargement factor k=2.0 to the mapping transformers 22-2 to 22-5.

Furthermore, the setting unit 212 supplies the five high-resolution directions supplied to the rotation processing units 211-1 to 211-5 and the enlargement factor k supplied to the mapping transformers 22-1 to 22-5 to the table generation unit 213.

The table generation unit 213 generates a table in which the information specifying the five high-resolution directions and the information specifying the enlargement factor k supplied from the setting unit 212 are grouped for each stream, and supplies the generated table to the transmitter 24 as auxiliary information (meta-information).

FIG. 23 illustrates an example of a table as auxiliary information generated by the table generation unit 213.

The information for specifying the high-resolution direction is defined by an azimuth angle $\theta$, an elevation angle $\varphi$, and a rotation angle $\psi$, and the information indicating the enlargement factor is defined by an enlargement factor k. The representation of the high-resolution direction by a combination of rotations of three axes of the azimuth angle $\theta$, the elevation angle $\varphi$, and the rotation angle $\psi$ enables for the description of any rotation. The enlargement factor k corresponds to the enlargement factor at the point where the resolution is highest, and the enlargement factor decreases as the distance from that point increases. The distribution of the enlargement factor can take various distributions depending on the viewport dependent projection mapping scheme.

In FIG. 23, ID1 to ID5 are identification information used to respectively identify the five encoded streams transmitted to the delivery server 13 and respectively correspond to the omnidirectional images 231-1 to 231-5 illustrated in FIG. 22.

The encoded stream of ID1 corresponds to the omnidirectional image 231-1 illustrated in FIG. 22 and indicates that an enlargement factor k=1.0 at the center of the image in setting the direction dir1 of FIG. 20 as the center of the image, that is, indicates that the image is an equirectangular image having a uniform resolution in all directions.

The encoded stream of ID2 corresponds to the omnidirectional image 231-2 illustrated in FIG. 22 and indicates that the direction dir1 of FIG. 20 is set as the center of the image and the image is an equirectangular image in which the pixels in the direction dir1 are enlarged at the enlargement factor k=2.0.

The encoded stream of ID3 corresponds to the omnidirectional image 231-3 illustrated in FIG. 22 and indicates that the direction dir2 of FIG. 20 is set as the center of the image and the image is an equirectangular image in which the pixels in the direction dir2 are enlarged at the enlargement factor k=2.0.

The encoded stream of ID4 corresponds to the omnidirectional image 231-4 illustrated in FIG. 22 and indicates that the direction dir3 of FIG. 20 is set as the center of the image and the image is an equirectangular image in which the pixels in the direction dir3 are enlarged at the enlargement factor k=2.0.

The encoded stream of ID5 corresponds to the omnidirectional image 231-5 illustrated in FIG. 22 and indicates that the direction dir4 of FIG. 20 is set as the center of the image and the image is an equirectangular image in which the pixels in the direction dir4 are enlarged at the enlargement factor k=2.0.

The transmitter 24 uploads (transmits) the auxiliary information supplied from the table generation unit 213 to the delivery server 13 in FIG. 1 together with the five encoded streams supplied from the encoders 23-1 to 23-5.

Moreover, the example of the generation apparatus 12 in FIG. 21 employs a configuration in which the number of high-resolution directions being set is determined in advance to four and each set of the rotation processing units 211, the mapping transformers 22, and the encoders 23 is provided in the generation apparatus 12 as five sets including four sets for high-resolution images and one set for uniform-resolution images. However, the number of each of the rotation processing units 211, the mapping transformers 22, and the encoders 23 can be variable corresponding to the number of high-resolution directions optionally determined by the setting unit 212.

In FIG. 21, a supply line for supplying predetermined data (high-resolution direction or enlargement factor) from the setting unit 212 to the rotation processing units 211-1 to 211-5 and the mapping transformers 22-1 to 22-5 is omitted.

(Exemplary Configuration of Delivery Server and Playback Apparatus)

Figure 24:
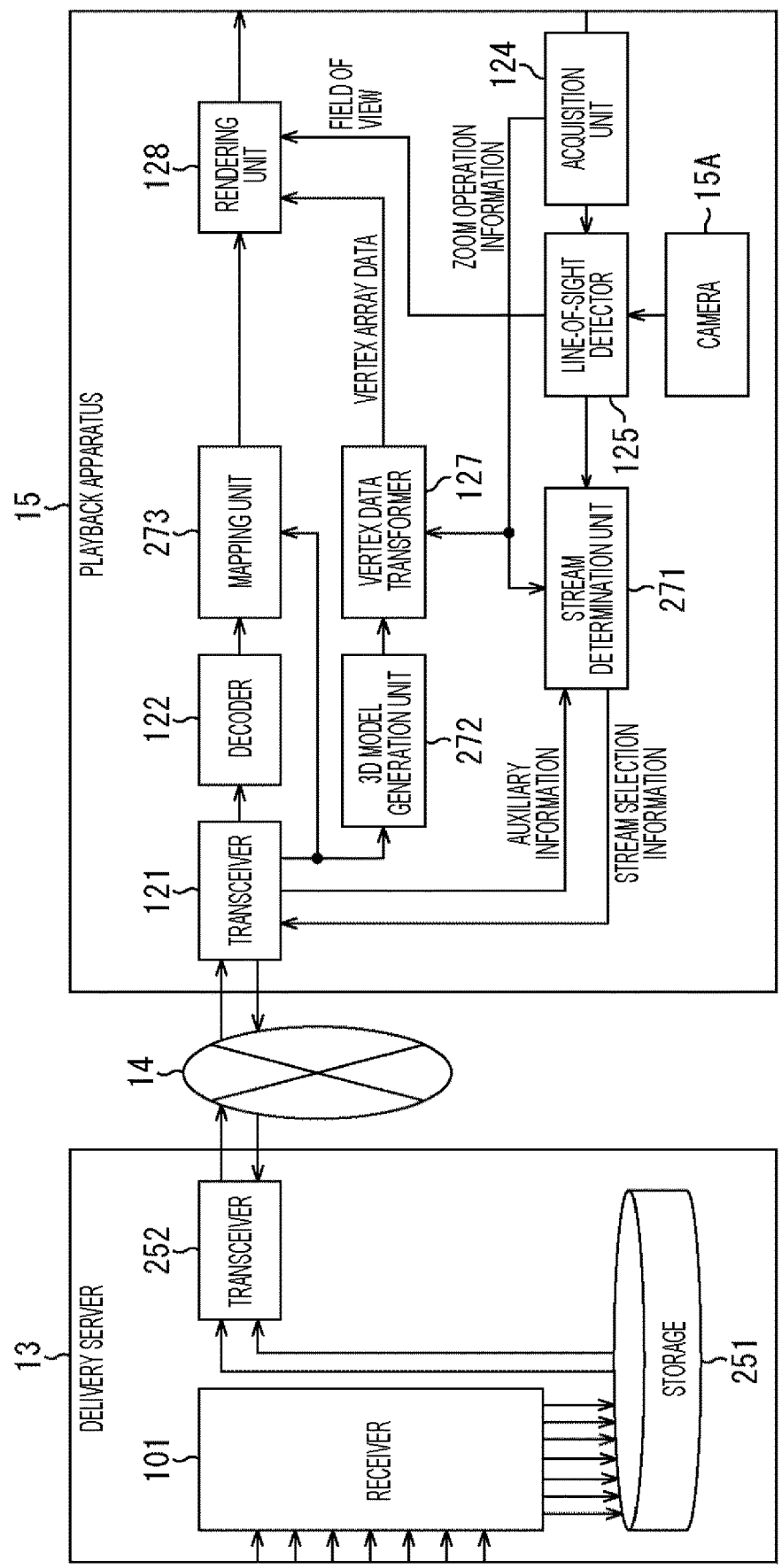
FIG. 24 is a block diagram illustrating an exemplary configuration of a delivery server and a playback apparatus according to the second embodiment.

FIG. 24 is a block diagram illustrating an exemplary configuration of the delivery server 13 and the playback apparatus 15 of the delivery system 10 according to the second embodiment.

In FIG. 24, the same reference numerals are given to the portions corresponding to FIG. 4, so the description of the portions will be appropriately omitted.

The delivery server 13 includes the receiver 101, a storage 251, and a transceiver 252.

The receiver 101 receives the five encoded streams and the auxiliary information uploaded from the generation apparatus 12 in FIG. 1 and supplies them to the storage 251.

The storage 251 stores the five encoded streams and the auxiliary information supplied from the receiver 101.

The transceiver 252 reads the auxiliary information stored in the storage 251 in response to a request from the playback apparatus 15 and transmits the auxiliary information to the playback apparatus 15 via the network 14.

In addition, the transceiver 252 reads a predetermined one of the five encoded streams stored in the storage 251 in response to a request from the playback apparatus 15 and transmits it to the playback apparatus 15 via the network 14. The one encoded stream transmitted from the transceiver 252 to the playback apparatus 15 is appropriately changed depending on the request from the playback apparatus 15.

Moreover, the change of the encoded stream to be transmitted is performed at the sync point. Thus, the encoded stream to be transmitted is changed in units of several frames to several tens of frames. In addition, as described above, the sync point is the same among the five encoded streams. Thus, the transceiver 252 is capable of easily switching the captured image to be played back in the playback apparatus 15 by switching the encoded stream to be transmitted at the sync point.

The playback apparatus 15 includes a camera 15A, a transceiver 121, a decoder 122, an acquisition unit 124, a line-of-sight detector 125, a vertex data transformer 127, a rendering unit 128, a stream determination unit 271, a 3D model generation unit 272, and a mapping unit 273.

Thus, comparing with the playback apparatus 15 according to the first embodiment, the playback apparatus 15 according to the second embodiment includes the 3D model generation unit 272 and the mapping unit 273 instead of the 3D model generation unit 126 and the mapping unit 123, respectively, and is additionally provided with the stream determination unit 271.

The stream determination unit 271 is supplied with the auxiliary information from the transceiver 121. In addition, the stream determination unit 271 is supplied with the zoom operation information from the acquisition unit 124, and is supplied with the viewer/listener's line-of-sight direction from the line-of-sight detector 125.

The stream determination unit 271 (selection unit) determines (selects) a predetermined one of the five encoded streams, which is obtainable from the delivery server 13, on the basis of the viewer/listener's line-of-sight direction, the zoom operation information, and the auxiliary information.

More specifically, the stream determination unit 271 determines the stream of ID1 in FIG. 23 as the request stream in the case where the zoom operation is not performed, and determines any stream of ID2 to ID5 corresponding to the viewer/listener's line-of-sight direction as a request stream in the case where the zoom operation is performed.

The stream determination unit 271 supplies stream selection information indicating the selected encoded stream to the transceiver 121. The transceiver 121 transmits the stream selection information from the stream determination unit 271 to the delivery server 13 via the network 14.

In a case where the encoded stream transmitted from the delivery server 13 is changed depending on the stream selection information, the transceiver 121 supplies stream information indicating the change of the encoded stream to the 3D model generation unit 272 and the mapping unit 273.

The 3D model generation unit 272 generates data of the 3D mesh model corresponding to the encoded stream transmitted from the delivery server 13 and supplies the data to the vertex data transformer 127. More specifically, the 3D model generation unit 272 generates vertex array data in which the coordinates (x, y, z) of each vertex in the vertex array data including the coordinates (x, y, z) of each vertex of the 3D model and the corresponding texture coordinates (u, v) are rotationally corrected on the basis of directions dir1 to dir4 indicating the high-resolution direction, and supplies it to the vertex data transformer 127.

The mapping unit 273 generates the texture data (R, G, B) corresponding to the texture coordinates (u, v) on the basis of the UV mapping model corrected so that the center of the omnidirectional image supplied from the decoder 122 has a high resolution at the enlargement factor k.

Moreover, the high-resolution direction and the enlargement factor k of the encoded stream being transmitted can be supplied from the stream determination unit 271 or can be supplied as a part of the stream information from the transceiver 121 on the basis of the contents included in the metadata of the encoded stream being transmitted.

Other components of the delivery server 13 and the playback apparatus 15 in FIG. 24 are similar to those of the delivery server 13 and the playback apparatus 15 in FIG. 4.

(Processing in Generation Apparatus)

Figure 25:
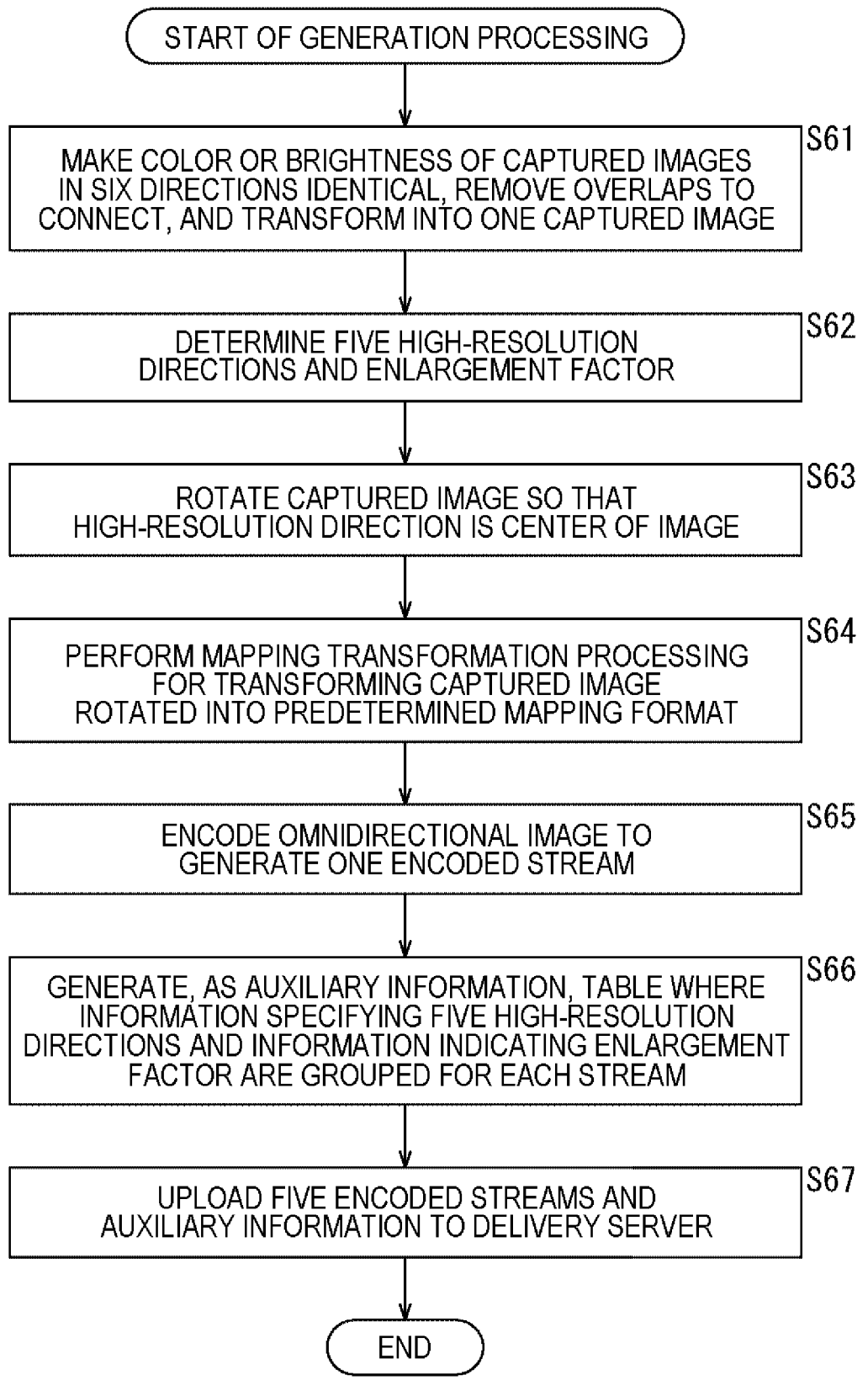
FIG. 25 is a flowchart illustrated to describe generation processing according to the second embodiment.

FIG. 25 is a flowchart illustrated to describe generation processing performed by the generation apparatus 12 in FIG. 21. This processing is started, in one example, when moving images in six directions captured by the six cameras 11A-1 to 11A-6 of the imaging apparatus 11 are supplied.

In step S61 as the first step, the stitching unit 21 makes colors or brightness of the captured images in the six directions supplied from the respective cameras 11A identical for each frame, removes overlaps to connect, and then transforms them into a single captured image. The stitching unit 21 generates, in one example, an equirectangular image as one captured image, and supplies the equirectangular image in frame units to the rotation processing unit 211.

In step S62, the setting unit 212 determines the five high-resolution directions and the enlargement factor. The setting unit 212 supplies the determined five high-resolution directions to the rotation processing units 211-1 to 22-5 one by one, and supplies the determined enlargement factor to the mapping units 22-1 to 22-5. Specifically, the direction dir1 in FIG. 20 is supplied to the rotation processing units 211-1 and 211-2, the direction dir2 in FIG. 20 is supplied to the rotation processing unit 211-3, and the direction dir3 in FIG. 20 is supplied to the rotation processing unit 211-4, and the direction dir4 in FIG. 20 is supplied to the rotation processing unit 211-4. For the enlargement factor, the enlargement factor k=1.0 is supplied to the mapping transformer 22-1, and the enlargement factor k=2.0 is supplied to the mapping transformers 22-2 to 22-5. In addition, the setting unit 212 also supplies the determined five high-resolution directions and the enlargement factor to the table generation unit 213.

In step S63, the rotation processing unit 211 rotates the captured image (e.g., an equirectangular image) of the frame unit that is supplied from the stitching unit 21 so that the high-resolution direction specified by the setting unit 212 is the center of the image.

In step S64, the mapping unit 22 performs the mapping transformation processing of transforming the captured image that is rotated by the rotation processing unit 211 into a mapping format for mapping to a predetermined 3D model. In the mapping transformation processing, mapping is performed so that the center of the captured image has the highest resolution depending on the enlargement factor k.

In step S65, the encoder 23 encodes the omnidirectional image supplied from the mapping unit 22 using a predetermined encoding scheme such as the MPEG-2 or AVC standard to generate one encoded stream. The encoder 23 supplies one encoded stream being generated to the transmitter 24.

The processing of steps S63 to S65 is executed in parallel in five sets of each of the rotation processing units 211, the mapping units 22, and the encoders 23, and a total of five encoded streams are supplied to the transmitter 24.

In step S66, the table generation unit 213 generates, as auxiliary information, a parameter table in which information used to specify five high-resolution directions and information indicating an enlargement factor are grouped for each stream, and supplies it to the transmitter 24.

In step S67, the transmitter 24 uploads a total of five encoded streams supplied from the five encoders 23 and the auxiliary information supplied from the table generation unit 213 to the delivery server 13.

(Description of Processing in Playback Apparatus)

Figure 26:
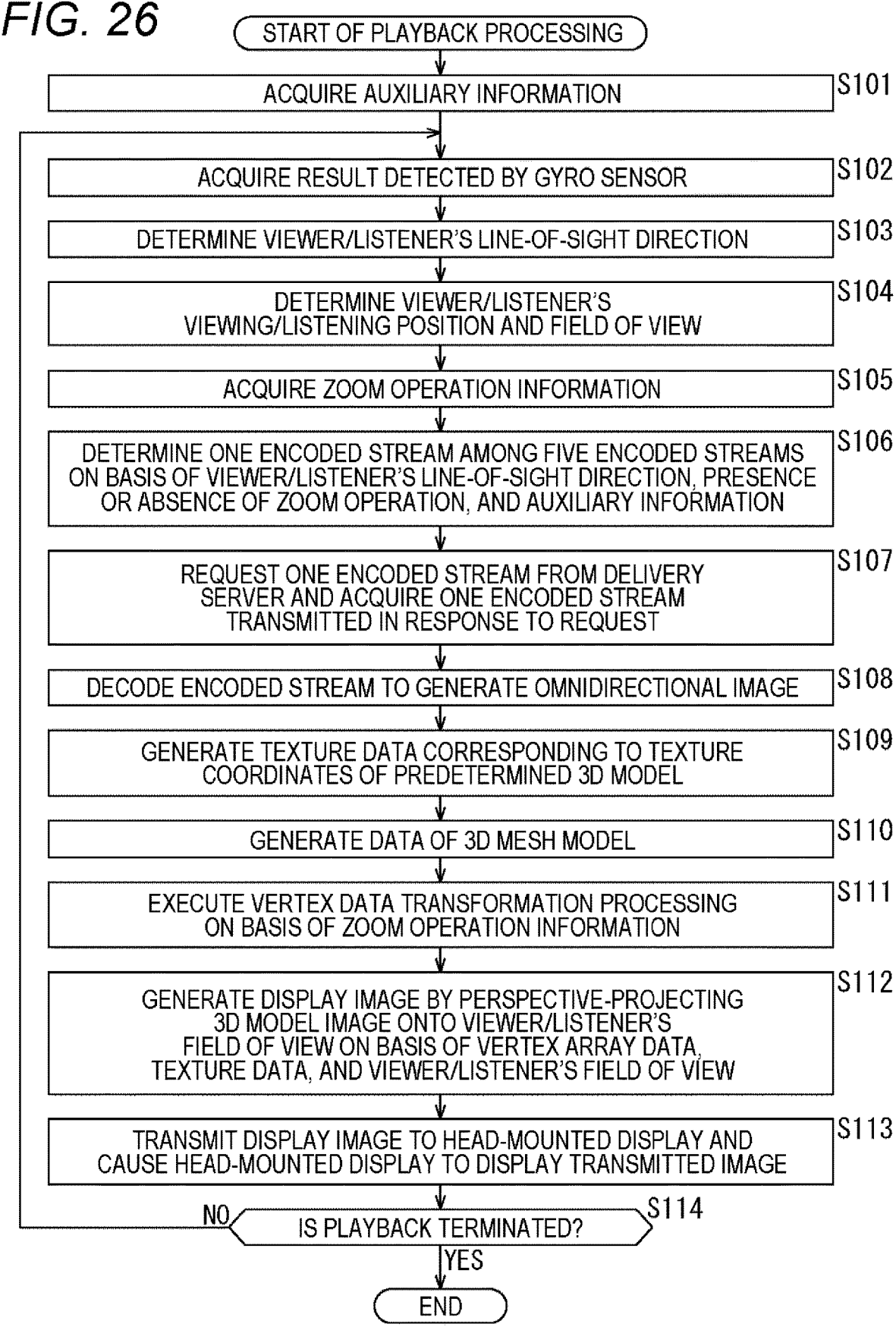
FIG. 26 is a flowchart illustrated to describe playback processing according to the second embodiment.

FIG. 26 is a flowchart illustrated to describe playback processing performed by the playback apparatus 15 in FIG. 24. This playback processing is started, in one example, when the playback apparatus 15 detects a power-on or a processing start operation.

In step S101 as the first step, the transceiver 121 requests auxiliary information from the delivery server 13 and receives the auxiliary information transmitted from the transceiver 252 of the delivery server 13 in response to the request. The transceiver 121 supplies the obtained auxiliary information to the stream determination unit 271.

In step S102, the acquisition unit 124 acquires the detection result of the gyro sensor 16B in FIG. 1 from the head-mounted display 16 and supplies the result to the line-of-sight detector 125.

In step S103, the line-of-sight detector 125 determines a viewer/listener's line-of-sight direction in the coordinate system of the 3D model on the basis of the detection result of the gyro sensor 16B that is to be supplied from the acquisition unit 124, and supplies the direction to the stream determination unit 271.

In step S104, the line-of-sight detector 125 determines the viewer/listener's viewing/listening position and field of view in the coordinate system of the 3D model and supplies them to the rendering unit 128. More specifically, the line-of-sight detector 125 acquires a captured image of the marker 16A from the camera 15A and detects a viewing/listening position in the coordinate system of the 3D model on the basis of the captured image. Then, the line-of-sight detector 125 determines the viewer/listener's field of view in the 3D model coordinate system on the basis of the detected viewing position and line-of-sight direction.

In step S105, the acquisition unit 124 acquires the zoom operation information from the head-mounted display 16, and supplies the information to the vertex data transformer 127 and the stream determination unit 271.

In step S106, the stream determination unit 271 determines (selects) one encoded stream among the five encoded streams, which is obtainable from the delivery server 13, on the basis of the viewer/listener's line-of-sight direction, the presence or absence of a zoom operation, and the auxiliary information. Then, the stream determination unit 271 supplies the transceiver 121 with stream selection information indicating the selected encoded stream.

In step S107, the transceiver 121 requests one encoded stream, which corresponds to the stream selection information supplied from the stream determination unit 271, from the delivery server 13 via the network 14, and acquires the one encoded stream transmitted from the transceivers 252 of the delivery server 13 in response to the request. The transceiver 121 supplies the obtained one encoded stream to the decoder 122. In addition, the transceiver 121 supplies stream information indicating that the stream is changed to the 3D model generation unit 272 and the mapping unit 273.

In step S108, the decoder 122 decodes the encoded stream supplied from the transceiver 121 to generate an omnidirectional image. The decoder 122 supplies the generated omnidirectional image to the mapping unit 273.

In step S109, the mapping unit 273 generates texture data (R, G, B) corresponding to the texture coordinates (u, v) of the predetermined 3D model using the omnidirectional image supplied from the decoder 122. In this event, the mapping unit 273 generates texture data (R, G, B) based on a UV mapping model corrected so that the center of the omnidirectional image has a high resolution at the enlargement factor k on the basis of the stream information supplied from the transceiver 121. Moreover, in the case where the enlargement factor k is 1.0, the texture data (R, G, B) is texture data with no enlargement/reduction, that is, uniform resolution. The mapping unit 273 supplies the texture data to the rendering unit 128 by storing the generated texture data in a texture buffer accessible by the rendering unit 128.

In step S110, the 3D model generation unit 272 generates data of a 3D mesh model in a virtual 3D space and supplies the data to the vertex data transformer 127. This data of the 3D mesh model is the vertex array data in which the coordinates (x, y, z) of each vertex of vertex array data including the coordinates (x, y, z) of each vertex of the 3D model and the corresponding texture coordinates (u, v) are rotationally corrected on the basis of the directions dir1 to dir4 indicating the high-resolution direction as illustrated in FIG. 7.

In step S111, the vertex data transformer 127 executes the vertex data transformation processing on the basis of the zoom operation information supplied from the acquisition unit 124. This vertex data transformation processing is similar to the processing executed in steps S38 to S42 of FIG. 17. Specifically, the vertex data transformer 127 supplies the vertex array data supplied from the 3D model generation unit 272 to the rendering unit 128 without transformation in the case where the zoom operation is not performed. On the other hand, in the case where a zoom operation is performed, the vertex data transformer 127 transforms the vertex array data of the orthogonal coordinate system supplied from the 3D model generation unit 272 into the cylindrical coordinate system, and performs mapping transformation $f_k$ corresponding to the zoom operation. Then, the vertex data transformer 127 returns the vertex array data in the cylindrical coordinate system to the orthogonal coordinate system again and supplies it to the rendering unit 128.

In step S112, the rendering unit 128 generates a display image by perspective-projecting the 3D model image onto the viewer/listener's field of view on the basis of the vertex array data supplied from the vertex data transformer 127 (the orthogonal coordinate transformation unit 143 thereof), the texture data (R, G, B) supplied from the mapping unit 273, and the viewer/listener's field of view supplied from the line-of-sight detector 125.

In step S113, the rendering unit 128 transmits the display image to the head-mounted display 16, which is caused to display it.

In step S114, the playback apparatus 15 determines whether to terminate the playback. In one example, in a case where the viewer/listener performs an operation to terminate the playback, the playback apparatus 15 determines to terminate the playback.

If it is determined in step S114 that the playback is not to be terminated, the processing returns to step S102, and the processing of steps S102 to S114 described above is repeated. On the other hand, if it is determined in step S114 that the playback is to be terminated, the playback processing ends.

The playback processing described above allows the stream determination unit 271 of the playback apparatus 15 to select a stream corresponding to the omnidirectional image 231-1 having the uniform resolution and to request it from the delivery server 13 in the case where the viewer/listener does not perform the zoom operation (enlargement operation). Then, an image obtained by perspective-projecting the spherical model to which the omnidirectional image 231-1 having the uniform resolution is affixed onto the viewer/listener's field of view is displayed on the head-mounted display 16 as a display image.

On the other hand, in the case where the viewer/listener performs the zoom operation (enlargement operation), the stream determination unit 271 of the playback apparatus 15 selects the directions dir1 to dir4 closest to the viewer/listener's line-of-sight direction, selects a stream corresponding to the omnidirectional image (one of the omnidirectional images 231-2 to 231-5) having the selected direction (one of the directions dir1 to dir4) as the high-resolution direction, and requests it from the delivery server 13. Then, an image obtained by perspective-projecting a spherical model to which the obtained omnidirectional image (one of the omnidirectional images 231-2 to 231-5) having a high resolution at the center of the image is affixed onto the viewer/listener's field of view is caused to be displayed on the head-mounted display 16 as a display image.

In the case where the viewer/listener performs the reduction operation, the vertex data transformation processing performed by the vertex data transformer 127 allows the display image to be generated by using the spherical model in which the omnidirectional image 231-1 having a uniform resolution is shrunk and affixed, which is similar to the first embodiment.

The delivery systems according to the first and second embodiments described above, in the case where the scaling operation is performed, only allows the vertex data transformer 127 to perform the vertex data transformation processing in which the five-element vertex array data of the coordinates (x, y, z) and the texture coordinates (u, v) is transformed into five-element vertex array data of the coordinates (x', y', z') and texture coordinates (u, v) corresponding to the enlargement factor k and is rearranged. The processing by the rendering unit 128 that generates a perspective projection image of the viewer/listener's field of view to look around from the inside of the 3D model is no different from the case where the scaling operation is not performed.

The vertex data transformer 127 sets a vertical direction (vertical direction z) and a horizontal rotation direction (azimuth angle θ) using the vertical direction as a rotation axis and performs the coordinate transformation processing independently for each direction, to perform enlargement/reduction on the omnidirectional image. In other words, the vertex data transformer 127 performs the mapping transformation $f_k$ that multiplies the horizontal rotation direction (azimuth angle θ) by k and multiplies the vertical direction (vertical direction z) by k.

By setting the z-axis of the orthogonal coordinate system (x, y, z) that is the vertical direction as the gravity direction, the plane at z=0 is a horizontal plane like the ground, and the gravity direction and the horizontal direction are kept before and after the coordinate transformation processing, so it is possible to prevent the occurrence of motion sickness due to the inclination of scenery. In other words, there is no mismatch between the rotation angle of the head and the rotation angle of the image, so it is possible to achieve enlargement/reduction display of the image while preventing the occurrence of motion sickness.

The enlargement factor k in the mapping transformation $f_k$ is continuously variable and can be changed even during playback of a moving image. The vertical direction is kept even when the enlargement factor is changed, so motion sickness is unlikely to occur. In the case where the viewer/listener performs the enlargement operation, the horizontal image is 360 degrees or more, but in the configuration that performs rendering so that the horizontal image is continuous in a normal case, all directions being recorded are viewable through extra rotation by the enlarged magnification. On the other hand, in the case where the reduction operation is performed, the horizontal image is 360 degrees or less, so it is possible to view the image around the entire circumference with less rotation of the neck.

3. Other Modifications (Other Examples of Encoded Stream)

In each of the above-described embodiments, the omnidirectional image to be transmitted as an encoded stream is an omnidirectional image of a 2D image displayed as the same image on the viewer/listener's right and left eyes, but it can be an omnidirectional image for a 3D image obtained by combining (packing) the omnidirectional image for the left eye and the omnidirectional image for the right eye.

Figure 27:
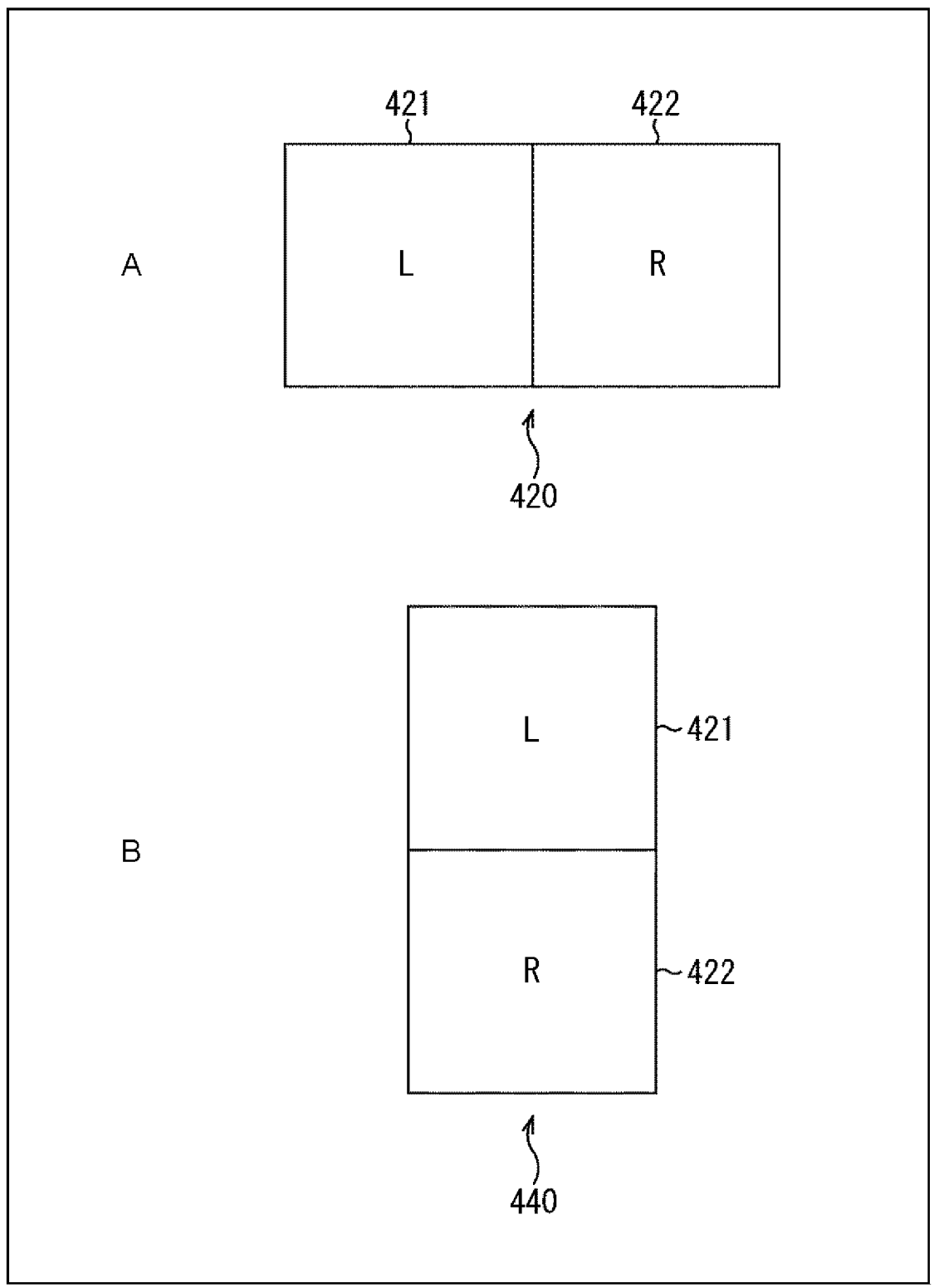
FIG. 27 is a diagram illustrated to describe a modification in which an encoded stream is an omnidirectional image for a 3D image.

More specifically, as illustrated in the portion A of FIG. 27, the omnidirectional image can be, in one example, a packed image 420 obtained by packing a left-eye omnidirectional image 421 and a right-eye omnidirectional image 422 in the lateral direction (horizontal direction).

Further, as illustrated in the portion B of FIG. 27, the omnidirectional image can be, in one example, a packed image 440 obtained by packing the left-eye omnidirectional image 421 and the right-eye omnidirectional image 422 in the longitudinal direction (perpendicular direction).

The left-eye omnidirectional image 421 is an image obtained by perspective-projecting the omnidirectional image of the left-eye viewpoint mapped to the sphere onto the field of view of the left eye with the center of the sphere as the focal point. In addition, the right-eye omnidirectional image 422 is an image obtained by perspective-projecting the omnidirectional image of the right-eye viewpoint mapped to the sphere onto the field of view of the right eye with the center of the sphere as the focal point.

In a case where the omnidirectional image is a packed image, the mapping unit 123 in FIG. 4 separates the packed image obtained as a result of decoding by the decoder 122 into a left-eye omnidirectional image and a right-eye omnidirectional image. Then, the mapping unit 123 generates texture data (R, G, B) for each of the left-eye viewpoint and the right-eye viewpoint, and the rendering unit 128 generates a display image using a 3D model image for each of the left-eye viewpoint and the right-eye viewpoint.

This makes it possible for the head-mounted display 16, in the case of allowing 3D display, to display the display images of the left-eye viewpoint and the right-eye viewpoint as a left-eye image and a right-eye image, respectively, resulting in displaying the image as 3D.

(Example of Live Streaming)

In each of the above-described embodiments, one or more encoded streams and auxiliary information generated by the generation apparatus 12 are once stored in the storage 102 or 251 of the delivery server 13, and then the delivery server 13 transmits the encoded stream and the auxiliary information to the playback apparatus 15 in response to a request from the playback apparatus 15.

However, one or more encoded streams and auxiliary information generated by the generation apparatus 12 can be delivered in real-time (live streaming) without being stored in the storage 102 or 251 of the delivery server 13. In this case, the data received through the receiver 101 of the delivery server 13 is immediately transmitted from the transceiver 103 or 252 to the playback apparatus 15.

(Other)

Furthermore, in the above-described embodiment, the captured image is a moving image, but it can be a still image. In addition, in the above-described embodiment, an example is described in which an omnidirectional image captured in 360 degrees (all directions) is used, but the technology according to the present disclosure is not limited to an image covering all directions, it is applicable to any wide-angle image (what is called panoramic images) in a range narrower than 360 degrees. Examples of the wide-angle image include a 360-degree (all directions) omnidirectional image, an omnidirectional image, all direction image, a 360-degree panoramic image, or the like.

The delivery system 10 can include a stationary display instead of the head-mounted display 16. In this case, the playback apparatus 15 does not have the camera 15A, and so the viewing/listening position and the line-of-sight direction are detected on the basis of information regarding the operation of the controller 16C by the viewer/listener.

Further, the delivery system 10 can include a mobile terminal instead of the playback apparatus 15 and the head-mounted display 16. In this case, the mobile terminal performs processing of the playback apparatus 15 except for the camera 15A, and causes a display image to be displayed on a display of the mobile terminal. The viewer/listener inputs the viewing/listening position and the line-of-sight direction by changing the attitude of the mobile terminal, and the mobile terminal acquires the input viewing/listening position and line-of-sight direction by causing the built-in gyro sensor to detect the attitude of the mobile terminal.

4. Example of Computer Configuration

The series of processes described above can be executed by hardware, and can also be executed in software. In the case of executing the series of processes by software, a program forming the software is installed on a computer. Herein, the term computer includes a computer built into special-purpose hardware, a computer able to execute various functions by installing various programs thereon, such as a general-purpose personal computer, for example, and the like.

Figure 28:
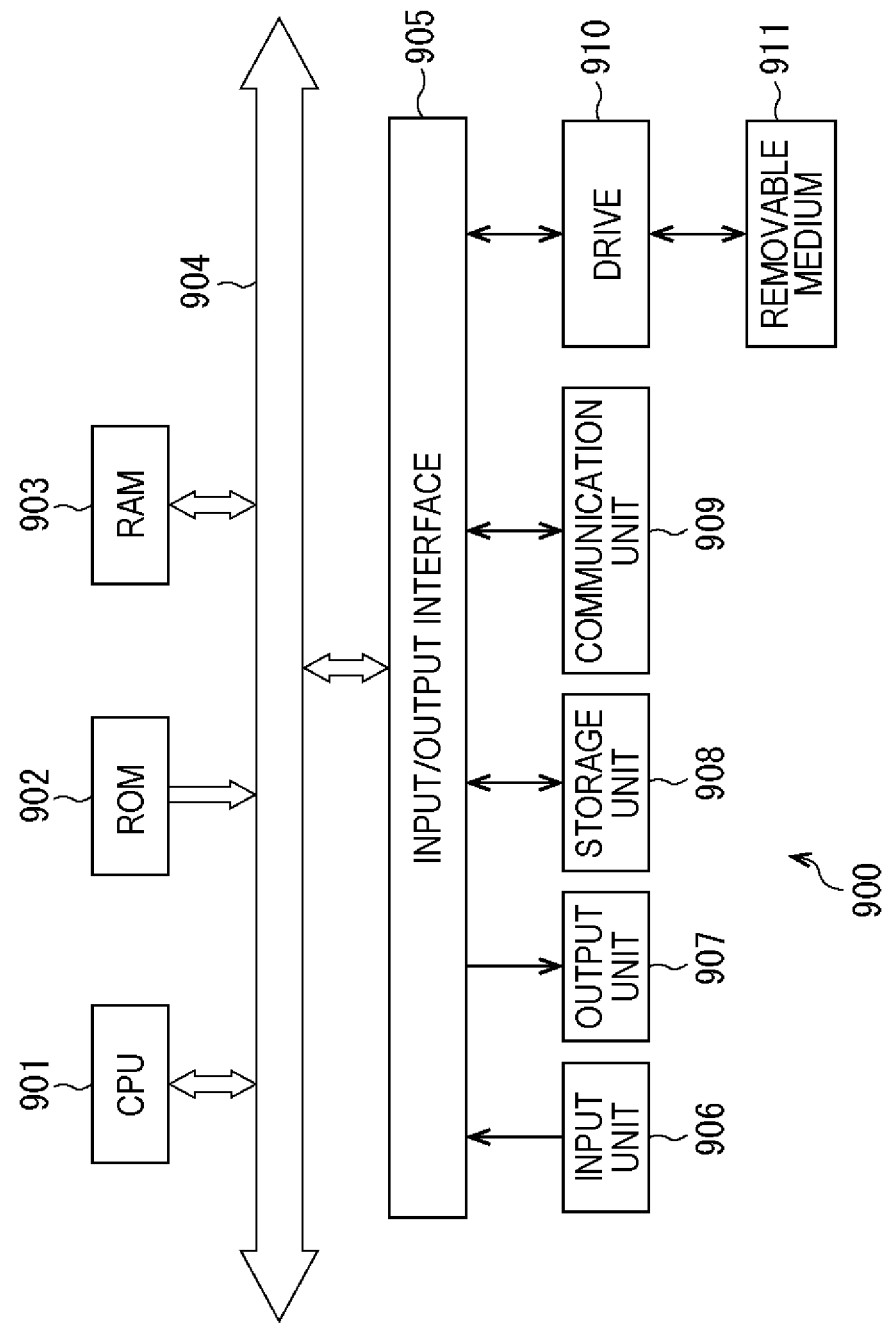
FIG. 28 is a block diagram illustrating an exemplary configuration of an embodiment of a computer to which the technology of the present disclosure is applied.

FIG. 28 is a block diagram illustrating an exemplary hardware configuration of a computer that executes the series of processes described above according to a program.

In the computer 900, a central processing unit (CPU) 901, read only memory (ROM) 902, and random access memory (RAM) 903 are interconnected by a bus 904.

Additionally, an input/output interface 905 is connected to the bus 904. An input unit 906, an output unit 907, a storage unit 908, a communication unit 909, and a drive 910 are connected to the input/output interface 905.

The input unit 906 includes a keyboard, a mouse, a microphone, and the like, for example. The output unit 907 includes a display, a speaker, and the like, for example. The storage unit 908 includes a hard disk, non-volatile memory, and the like, for example. The communication unit 909 includes a network interface, for example. The drive 910 drives a removable medium 911 such as a magnetic disk, an optical disc, a magneto-optical disc, or semiconductor memory.

In a computer 900 configured as above, the series of processes described above are performed by having the CPU 901 load a program stored in the storage unit 908 into the RAM 903 via the input/output interface 905 and the bus 904, and execute the program, for example.

The program executed by the computer 900 (the CPU 901) can be recorded on, for example, the removable medium 911 serving as a package medium or the like for supply. In addition, the program can be supplied via a wired or wireless transmission medium such as a local area network, the Internet, or digital satellite broadcast.

In the computer 900, the program can be installed to the storage unit 908 via the input/output interface 905 by mounting the removable medium 911 on the drive 910. In addition, the program can be received by the communication unit 909 via a wired or wireless transmission medium and can be installed in the storage unit 908. Additionally, the program can be installed in advance in the ROM 902 or the storage unit 908.

Note that the program executed by the computer 900 may be a program which is processed chronologically in the sequence described in the present specification or may be a program which is processed in parallel or at a necessary timing such as the calling time.

Note that, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a single device including a plurality of modules within a single casing.

Further, an embodiment of the disclosure is not limited to the embodiments described above, and various changes and modifications may be made without departing from the scope of the disclosure.

For example, it is possible to adapt a whole or a part of a plurality of embodiments described above.

For example, the present disclosure can adopt a configuration of cloud computing which processes by allocating and connecting one function by a plurality of apparatuses through a network.

Further, each step described by the above-mentioned flow charts can be executed by one apparatus or by allocating a plurality of apparatuses.

In addition, in the case where a plurality of processes is included in one step, the plurality of processes included in this one step can be executed by one apparatus or by sharing a plurality of apparatuses.

Note that the advantageous effects described in the present specification are merely examples and are not limitative, and other advantageous effects than those described in the present specification may be achieved.

Further, the present disclosure may include the following configuration.

(1)
A playback apparatus including:
a 3D model generation unit configured to generate a 3D model for enlargement/reduction in a case of selecting enlargement/reduction of a wide-angle image.

(2)
The playback apparatus according to (1),
in which the 3D model generation unit generates the 3D model for enlargement/reduction by setting a vertical direction and a horizontal rotation direction using the vertical direction as an axis and performing coordinate transformation processing independently for each direction.

(3)
The playback apparatus according to (2),
in which the 3D model generation unit performs the coordinate transformation processing on the vertical direction and the horizontal rotation direction at an identical enlargement factor.

(4)
The playback apparatus according to any one of (1) to (3),
in which the 3D model generation unit generates the 3D model for enlargement/reduction by performing coordinate transformation processing of transforming an orthogonal coordinate system into a cylindrical coordinate system and returning the cylindrical coordinate system to the orthogonal coordinate system.

(5)
The playback apparatus according to any one of (1) to (4),
in which the 3D model generation unit generates the 3D model for enlargement/reduction, upon subjecting to enlargement of k times, in such a way that one circling round of an original wide-angle image is capable of being viewed in a case where a viewer/listener rotates k revolutions in a horizontal rotation direction.

(6)
The playback apparatus according to any one of (1) to (5),
in which the 3D model generation unit generates the 3D model for enlargement/reduction, upon subjecting to reduction of 1/k times, in such a way that circling round k times of an original wide-angle image is capable of being viewed in a case where a viewer/listener rotates one revolution in a horizontal rotation direction.

(7)
The playback apparatus according to any one of (1) to (4),
in which the 3D model generation unit generates the 3D model for enlargement/reduction, upon subjecting to enlargement of k times, in such a way of cropping an image exceeding 360 degrees.

(8)
The playback apparatus according to any one of (1) to (7),
in which the 3D model for enlargement/reduction is a spherical model.

(9)
The playback apparatus according to any one of (1) to (7),
in which the 3D model for enlargement/reduction is a cubic model.

(10)
The playback apparatus according to any one of (1) to (9), further including:
a selection unit configured to select a first wide-angle image having a uniform resolution in all directions or a second wide-angle image having a high resolution in a predetermined direction in response to a wide-angle image enlargement/reduction operation by a viewer/listener,
in which the 3D model generation unit generates the 3D model for enlargement/reduction using the selected first wide-angle image or second wide-angle image.

(11)
The playback apparatus according to (10),
in which the 3D model generation unit generates the 3D model for enlargement/reduction using the second wide-angle image in a case of performing an operation of enlarging the wide-angle image.

(12)
A playback method including:
generating, by a playback apparatus, a 3D model for enlargement/reduction in a case of selecting enlargement/reduction of a wide-angle image.

(13)
A generation apparatus including:
a wide-angle image generation unit configured to generate a wide-angle image mapped to a predetermined 3D model for use in a playback apparatus including a 3D model generation unit configured to generate a 3D model for enlargement/reduction in a case of selecting enlargement/reduction of the wide-angle image.

(14)
The generation apparatus according to (13),
in which the wide-angle image generation unit generates, as the wide-angle image, a first wide-angle image having a uniform resolution in all directions.

(15)

The generation apparatus according to (14), in which the wide-angle image generation unit further generates, as the wide-angle image, a second wide-angle image having a high resolution in a predetermined direction.

(16)

The generation apparatus according to (15), further including:

an auxiliary information generation unit configured to generate, as auxiliary information, information used to specify a high-resolution direction of the second wide-angle image and information used to specify an enlargement factor indicating a high-resolution ratio; and a transmission unit configured to transmit the first wide-angle image, the second wide-angle image, and the auxiliary information to the playback apparatus.

(17)

The generation apparatus according to any one of (13) to (16), in which the predetermined 3D model is a spherical model.

(18)

The generation apparatus according to any one of (13) to (16), in which the predetermined 3D model is a cubic model.

(19)

A generation method including:

generating, by a generation apparatus, a wide-angle image mapped to a predetermined 3D model for use in a playback apparatus including a 3D model generation unit configured to generate a 3D model for enlargement/reduction in a case of selecting enlargement/reduction of the wide-angle image.

REFERENCE SIGNS LIST

10 Delivery system
12 Generation apparatus
13 Delivery server
15 Playback apparatus
16 Head-mounted display
22 Mapping transformer
23 Encoder
24 Transmitter
121 Transceiver
122 Decoder
123 Mapping unit
124 Acquisition unit
125 Line-of-sight detector
126 3D model generation unit
127 Vertex data transformer
128 Rendering unit
141 Cylindrical coordinate transformation unit
142 Scaling unit
143 Orthogonal coordinate transformation unit
151 Rendering unit
211 Rotation processing unit
212 Setting unit
213 Table generation unit
271 Stream determination unit
272 3D model generation unit
273 Mapping unit
900 Computer
901 CPU
902 ROM
903 RAM
906 Input unit
907 Output unit
908 Storage unit
909 Communication unit
910 Drive

The invention claimed is:

1. A playback apparatus comprising:
a 3D model generation unit configured to generate a 3D model for enlargement/reduction in a case of selecting enlargement/reduction of a wide-angle image,
wherein the 3D model generation unit generates the 3D model for enlargement/reduction by setting a vertical direction and a horizontal rotation direction using the vertical direction as an axis, performing coordinate transformation processing on the vertical direction on a basis of a distance in the vertical direction, and performing the coordinate transformation processing on the horizontal rotation direction on a basis of an azimuth angle, so that the 3D model for enlargement/reduction is allowed to have no dependency between the vertical direction and the horizontal rotation direction.

2. The playback apparatus according to claim 1,
wherein the 3D model generation unit performs the coordinate transformation processing on the vertical direction and the horizontal rotation direction at an identical enlargement factor.

3. The playback apparatus according to claim 1,
wherein the 3D model generation unit generates the 3D model for enlargement/reduction by performing coordinate transformation processing of transforming an orthogonal coordinate system into a cylindrical coordinate system and returning the cylindrical coordinate system to the orthogonal coordinate system.

4. The playback apparatus according to claim 1,
wherein the 3D model generation unit generates the 3D model for enlargement/reduction, upon subjecting to enlargement of k times, in such a way that one circling round of an original wide-angle image is capable of being viewed in a case where a viewer/listener rotates k revolutions in a horizontal rotation direction.

5. The playback apparatus according to claim 1,
wherein the 3D model generation unit generates the 3D model for enlargement/reduction, upon subjecting to reduction of 1/k times, in such a way that circling round k times of an original wide-angle image is capable of being viewed in a case where a viewer/listener rotates one revolution in a horizontal rotation direction.

6. The playback apparatus according to claim 1,
wherein the 3D model generation unit generates the 3D model for enlargement/reduction, upon subjecting to enlargement of k times, in such a way of cropping an image exceeding 360 degrees.

7. The playback apparatus according to claim 1, further comprising:
a selection unit configured to select a first wide-angle image having a uniform resolution in all directions or a second wide-angle image having a high resolution in a predetermined direction in response to a wide-angle image enlargement/reduction operation by a viewer/listener,
wherein the 3D model generation unit generates the 3D model for enlargement/reduction using the selected first wide-angle image or second wide-angle image.

8. The playback apparatus according to claim 7,
wherein the 3D model generation unit generates the 3D model for enlargement/reduction using the second wide-angle image in a case of performing an operation of enlarging the wide-angle image.

9. A playback method comprising:

generating, by a playback apparatus, a 3D model for enlargement/reduction in a case of selecting enlargement/reduction of a wide-angle image, by setting a vertical direction and a horizontal rotation direction using the vertical direction as an axis, performing coordinate transformation processing on the vertical direction on a basis of a distance in the vertical direction, and performing the coordinate transformation processing on the horizontal rotation direction on a basis of an azimuth angle, so that the 3D model for enlargement/reduction is allowed to have no dependency between the vertical direction and the horizontal rotation direction upon generation of the 3D model for enlargement/reduction.

\* \* \* \* \*